US007786079B2

(12) United States Patent
Von Nussbaum et al.

(10) Patent No.: US 7,786,079 B2
(45) Date of Patent: Aug. 31, 2010

(54) SUBSTITUTED NONADEPSIPEPTIDES

(75) Inventors: Franz Von Nussbaum, Duesseldorf (DE); Nina Brunner, Essen (DE); Rainer Endermann, Wuppertal (DE); Chantal Fuerstner, Muelheim An der Ruhr (DE); Elke Hartmann, Wuppertal (DE); Jacques Ragot, Duesseldorf (DE); Guido Schiffer, Wuppertal (DE); Joachim Schuhmacher, Wuppertal (DE); Niels Svenstrup, Velbert (DE); Joachim Telser, Wuppertal (DE); Sonja Anlauf, Wuppertal (DE); Michael-Alexander Bruening, Berlin (DE)

(73) Assignee: AiCuris GmbH & Co. KG., Wuppertal (DE)

( * ) Notice: Subject to any disclaimer, the term of this patent is extended or adjusted under 35 U.S.C. 154(b) by 141 days.

(21) Appl. No.: 11/788,590

(22) Filed: Apr. 19, 2007

(65) Prior Publication Data

US 2008/0058251 A1 Mar. 6, 2008

Related U.S. Application Data

(63) Continuation of application No. PCT/EP2005/010857, filed on Oct. 8, 2005.

(30) Foreign Application Priority Data

Oct. 20, 2004 (DE) ........................ 10 2004 051 025

(51) Int. Cl.
*A61K 38/12* (2006.01)
*C07K 7/54* (2006.01)
(52) U.S. Cl. .......................................... 514/9; 530/317
(58) Field of Classification Search ........................ None
See application file for complete search history.

(56) References Cited

U.S. PATENT DOCUMENTS

| 4,754,018 | A | 6/1988 | Tymiak et al. |
| 6,380,156 | B1 | 4/2002 | Rinehart et al. |
| 7,056,942 | B2 * | 6/2006 | Hildesheim et al. ......... 514/411 |
| 7,368,424 | B2 | 5/2008 | Von Nussbaum et al. |
| 7,531,507 | B2 | 5/2009 | Von Nussbaum et al. |
| 2005/0075281 | A1 | 4/2005 | Von Nussbaum et al. |
| 2005/0272646 | A1 | 12/2005 | Koteva et al. |
| 2006/0264358 | A1 | 11/2006 | Von Nussbaum et al. |
| 2008/0051424 | A1 | 2/2008 | Von Nussbaum et al. |
| 2008/0058253 | A1 | 3/2008 | Von Nussbaum et al. |
| 2008/0070884 | A1 | 3/2008 | Von Nussbaum et al. |
| 2009/0105119 | A1 | 4/2009 | Von Nussbaum et al. |

FOREIGN PATENT DOCUMENTS

| DE | 10 2004 0534 | 5/2006 |
| EP | 0 196 042 | 10/1986 |
| JP | 01132600 | 5/1989 |
| WO | WO-01/05814 | 1/2001 |
| WO | WO 2004/099239 | 11/2004 |
| WO | WO-2006/048156 | 5/2006 |

OTHER PUBLICATIONS vant Hof et al. (Biol Chem (2001) v382 pp. 597-619).*
Hingley (retrieved from http://www.fda.gov/FDAC/features/1998/398_alz.html on Jan. 7, 2009; 6 pages).*
Vippagunta et al (Adv. Drug Delivery Rev. v48 2001 pp. 3-26).*
Translation of the International Preliminary Report on Patentability for PCT/EP2005/010857, 11 pages.
Baquero, J. Antimicrob. Chemother. (1997) 39 (Suppl. A):1-6.
Bonner et al., The Journal of Antibiotics (1988) 41:1745-1751.
Egner and Bradley, Tetrahedron (1997) 53(41):14021-14030.
Goldrick, "First Reported Case of VRSA in the United States" Am. J. Nurs. (2002) 102(11):17.
Green, Expert Opinion Ther. Targets (2002) 6:1-19.
International Search Report for PCT/EP2005/010857, mailed on Mar. 27, 2006, 4 pages.
Johnson et al., J. Hosp. Infect. (2001) 49 (Suppl. A):S3-S11.
O'Sullivan et al., The Journal of Antibiotics (1988) 41:1740-1744.
Shoji et al., The Journal of Antibiotics (1988) 41:713-718.
Tymiak et al., J. Org. Chem. (1989) 54:1149-1157.
Alker et al., Tetrahedron (1998) 54:6089-6098.
Anderson and McGregor, J Am Chem Soc (1957) 79:6180-6183.
Bacterial Urinary Tract Infections from the Merck Manual, 8 pages.
Barret et al., Tetrahedron Lett (2001) 42(4):703-705.
Belokon et al., Tetrahedron: Asymmetry (2001) 12:481-485.
Blackburn et al., Drug Metabolism and Disposition (1993) 21(4):573-579.
Bull et al., J Chem Soc Perkin Trans (2001) 1:3281-3287.
Cardillo et al., Synlett (1999) 1727-1730.
Cellulitis from the Merck Manual, 3 pages.
Cohen et al., J Am Chem Soc (2004) 124:2534-2543.
Cystic Fibrosis from the Merck Manual, 7 pages.
Dikler et al., J Mass Spectrometry (1997) 32:1337-1349.
Echner et al., Liebigs Ann Chem (1988) 1095-1098.
English Translation of the International Preliminary Report on Patentability for PCT/EP2005/010856, issued on Apr. 24, 2007, 10 pages.
Harada et al., J of Chrom (2001) 932:75-81.
International Search Report for PCT/EP2005/011451, mailed on Feb. 27, 2006, 4 pages.
International Search Report for PCT/EP2007/000645, mailed on May 7, 2007, 4 pages.
International Search Report and Written Opinion for PCT/EP2007/003303, dated Jul. 19, 2007, 16 pages.
International Search Report and Written Opinion for PCT/EP2007/003313, dated Jul. 20, 2007, 10 pages.
IUPAC, Nomenclature and Symbolism for Amino Acids and Peptides, Names and Symbols for Derivatives of Named Peptides, Section 3AA-22 (Recommendations 1983-1992).
Jetten et al., Tetrahedron Lett (1991) 32:6025-6028.

(Continued)

*Primary Examiner*—Anish Gupta
*Assistant Examiner*—Ronald T Niebauer
(74) *Attorney, Agent, or Firm*—Morrison & Foerster LLP

(57) ABSTRACT

The invention relates to nonadepsipeptides and methods for their preparation and their use for the production of medicaments for the treatment and/or prophylaxis of diseases, in particular bacterial infectious diseases.

11 Claims, No Drawings

OTHER PUBLICATIONS

Jiang et al., J Am Chem Soc (2003) 125:1877-1887.
Kalvin et al., J Org Chem (1985) 50(13):2259-2263.
Kato et al., J Antibiot (1988) 41:719-725.
Lee et al., Tetrahedron (2001) 57:2139-2145.
Maki et al., Antimicrob Agents and Chemotherapy (2001) 45(6):1823-1827.
Mattingly et al., J Org Chem (1983) 48:3556-3559.
Merget et al., Organomet Chem (2001) 628:183-194.
Merino et al., Tetrahedron: Asymmetry (1998) 9:629-646.
Murakami et al., Tetrahedron (2000) 56(46):9121-9128.
Neises et al., Org Synth (1985) 63:183-187.
Nomenclature and Symbolism for Amino Acids and Peptides (Recommendations 1983) Biochemical Journal (1984) 219:345-373.
Norman et al., J Org Chem (1998) 63(15):5288-5294.
Oliyai et al., Pharm Res (1995) 12(3):323-328.
Palomo et al., Tetrahedron Lett (2001) 42:8955-8957.
Panico et al., eds., A Guide to IUPAC Nomenclature of Organic Compounds, Blackwell Science LTD., 1993, pp. 1-190 (Recommendations 1993).
Rane et al., Tetrahedron Lett (1993) 34(20):3201-3204.
Rao et al., Tetrahedron Lett (1991) 32:4393-4396.
Schuhmacher et al., J Pharm Sci (2004) 93:816-830.
Seebach et al., Helv Chim Acta (1996) 79:913-941.
Shemyakin et al., Esperienta (1966) 22(8):535-536.
Tenover, Am J Infect Control (2006) 34:S3-S10.
Thornber, Chem Soc Rev (1979) 8(4):563-580.
Translation of the International Preliminary Report on Patentability for PCT/EP2005/011451, mailed Jul. 12, 2007, 8 pages.
Translation of the International Preliminary Report on Patentability for PCT/EP2005/010858, issued Apr. 24, 2007, 5 pages.
Translation of the International Preliminary Report on Patentability for PCT/EP2007/000645, issued Sep. 9, 2008, 9 pages.
Ulhaq et al., Bioorg Med Chem (1999) 7(9):1787-1796.
U.S. Appl. No. 10/840,749, filed on May 6, 2004 [Von Nussbaum et al.].
Preliminary Amendment for U.S. Appl. No. 10/840,749, filed Dec. 17, 2004, 15 pages.
Restriction Requirement for U.S. Appl. No. 10/840,749, mailed Dec. 5, 2005, 7 pages.
Request for Extension of Time and Response to Restriction Requirement for U.S. Appl. No. 10/840,749, filed May 8, 2005, 2 pages.
Non-Final Office Action for U.S. Appl. No. 10/840,749, mailed on Aug. 8, 2006, 7 pages.
Amendment in Response to Non-Final Office Action for U.S. Appl. No. 10/840,749, filed on Nov. 8, 2006, 14 pages.
Non-Final Office Action for U.S. Appl. No. 10/840,749, mailed on Feb. 22, 2007, 11 pages.
Terminal Disclaimer for U.S. Appl. No. 10/840,749, filed on Jun. 22, 2007, 1 page.
Amendment in Response to Non-Final Office Action for U.S. Appl. No. 10/840,749, filed on Jun. 22, 2007, 16 pages.
Supplemental Amendment in Response to Non-Final Office Action for U.S. Appl. No. 10/840,749, filed on Nov. 20, 2007, 15 pages.
Notice of Allowance for U.S. Appl. No. 10/840,749, mailed on Dec. 3, 2007, 6 pages.
U.S. Appl. No. 11/267,063, filed Nov. 4, 2005 [Von Nussbaum et al.].
Preliminary Amendment for U.S. Appl. No. 11/267,063, filed on Jul. 13, 2006, 7 pages.
Restriction Requirement for U.S. Appl. No. 11/267,063, mailed on Apr. 12, 2007, 8 pages.
Amendment in Response to Non-Final Office Action for U.S. Appl. No. 11/267,063, filed on Jul. 11, 2007, 8 pages.
Non-Final Office Action for U.S. Appl. No. 11/267,063, mailed on Aug. 17, 2007, 18 pages.
Amendment in Response to Non-Final Office Action for U.S. Appl. No. 11/267,063, filed Jan. 15, 2008, 9 pages.
Non-Final Office Action for U.S. Appl. No. 11/267,063, mailed on Apr. 14, 2008, 8 pages.
Interview Summary for U.S. Appl. No. 11/267,063, mailed on Aug. 6, 2008, 4 pages.
Amendment in Response to Non-Final Office Action for U.S. Appl. No. 11/267,063, filed Sep. 8, 2008, 8 pages.
Notice of Allowance for U.S. Appl. No. 11/267,063, mailed on Dec. 30, 2008, 7 pages.
U.S. Appl. No. 11/788,649, filed on Apr. 20, 2007 [Von Nussbaum et al.].
Restriction Requirement for U.S. Appl. No. 11/788,649, mailed on Jul. 24, 2008, 10 pages.
Response to Restriction Requirement for U.S. Appl. No. 11/788,649, filed on Sep. 19, 2008, 5 pages.
Non-Final Office Action for U.S. Appl. No. 11/788,649, mailed on Jan. 26, 2009, 15 pages.
Amendment for U.S. Appl. No. 11/788,649, filed on Jun. 26, 2009, 19 pages.
U.S. Appl. No. 11/788,690, filed on Apr. 19, 2007 [Von Nussbaum et al.].
Restriction Requirement for U.S. Appl. No. 11/788,690, mailed on Mar. 23, 2009, 12 pages.
Response to Restriction Requirement for U.S. Appl. No. 11/788,690, filed on Apr. 16, 2009, 6 pages.
U.S. Appl. No. 11/800,495, filed on May 4, 2007 [Von Nussbaum et al.].
Restriction Requirement for U.S. Appl. No. 11/800,495, mailed on Jun. 19, 2008, 7 pages.
Response to Restriction Requirement for U.S. Appl. No. 11/800,495, filed on Aug. 19, 2008, 33 pages.
Restriction Requirement for U.S. Appl. No. 11/800,495, mailed on Dec. 8, 2008, 12 pages.
Response to Restriction Requirement for U.S. Appl. No. 11/800,495, filed on Jan. 8, 2009, 5 pages.
Non-Final Office Action for U.S. Appl. No. 11/800,495, mailed on Apr. 22, 2009, 14 pages.
U.S. Appl. No. 12/180,507, filed on Jul. 25, 2008 [Von Nussbaum et al.].
U.S. Appl. No. 12/249,880, filed on Oct. 10, 2008 [Von Nussbaum et al.].
U.S. Appl. No. 12/249,888, filed on Oct. 10, 2008 [Von Nussbaum et al.].

* cited by examiner

SUBSTITUTED NONADEPSIPEPTIDES

CROSS-REFERENCE TO RELATED APPLICATIONS

This application is a continuation of pending international application PCT/EP2005/010857, filed Oct. 8, 2005, designating US, which claims priority from German patent application DE 10 2004 051 025.3, filed Oct. 20, 2004. The contents of the above-referenced applications are incorporated herein by this reference in their entirety.

Reference to Sequence Listing Submitted Via EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 584212004801Seqlist.txt | Oct. 23, 2009 | 747 bytes |

BACKGROUND OF THE INVENTION

The invention relates to nonadepsipeptides and methods for their preparation, as well as to their use for the production of medicaments for the treatment and/or prophylaxis of diseases, in particular bacterial infectious diseases.

The bacterial cell wall is synthesized by a number of enzymes (cell wall biosynthesis) and is essential for the survival and reproduction of microorganisms. The structure of this macromolecule, as well as the proteins involved in its synthesis, are highly conserved within the bacteria. On account of its essential nature and uniformity, cell wall biosynthesis is an ideal point of attack for novel antibiotics (D. W. Green, The bacterial cell wall as a source of antibacterial targets, *Expert Opin. Ther. Targets*, 2002, 6, 1-19).

Vancomycin and penicillins are inhibitors of the bacterial cell wall biosynthesis and represent successful examples of the antibiotic potency of this principle of action. They have been employed for several decades clinically for the treatment of bacterial infections, especially with Gram-positive pathogens. Owing to the growing occurrence of resistant microorganisms, e.g. methicillin-resistant staphylococci, penicillin-resistant pneumococci and vancomycin-resistant enterococci (F. Baquero, Gram-positive resistance: challenge for the development of new antibiotics, *J. Antimicrob. Chemother.*, 1997, 39, Suppl A: 1-6; A. P. Johnson, D. M. Livermore, G. S. Tillotson, Antimicrobial susceptibility of Gram-positive bacteria: what's current, what's anticipated?, *J. Hosp. Infect.*, 2001, (49), Suppl A: 3-11) and recently also for the first time vancomycin-resistant staphylococci (B. Goldrick, First reported case of VRSA in the United States, *Am. J. Nurs.*, 2002, 102, 17), these substances are increasingly losing their therapeutic efficacy.

The present invention describes a novel class of cell wall biosynthesis inhibitors without cross resistances to known classes of antibiotics.

The natural product lysobactin and some derivatives are described as having antibacterial activity in U.S. Pat. No. 4,754,018. The isolation and antibacterial activity of lysobactin is also described in EP-A-196 042 and JP 01132600. WO04/099239 describes derivatives of lysobactin having antibacterial activity.

The antibacterial activity of lysobactin and katanosin A is furthermore described in O'Sullivan, J. et al., *J. Antibiot.* 1988, 41, 1740-1744, Bonner, D. P. et al., *J. Antibiot.* 1988, 41, 1745-1751, Shoji, J. et al., *J. Antibiot.* 1988, 41, 713-718 and Tymiak, A. A. et al., *J. Org. Chem.* 1989, 54, 1149-1157.

SUMMARY OF THE INVENTION

It is one object of the present invention to provide alternative compounds having comparable or improved antibacterial activity, better solubility and better tolerability, e.g. lower nephrotoxicity, for the treatment of bacterial diseases in humans and animals.

The invention relates to compounds of formula (I)

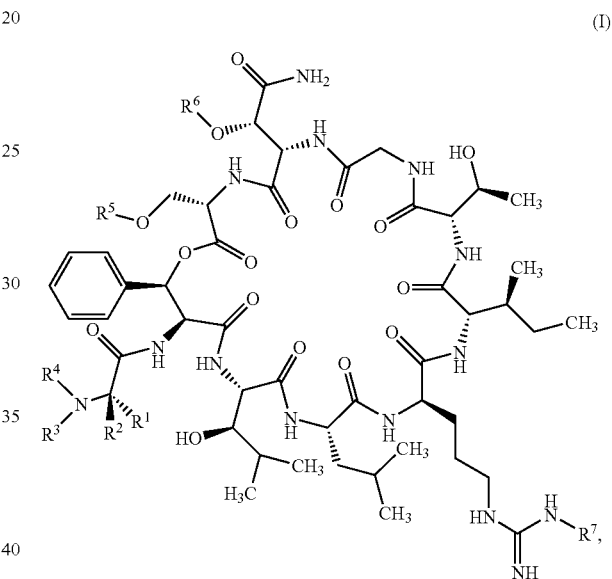

in which $R^1$ represents hydrogen, $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, $R^2$ represents hydrogen or $C_1$-$C_4$-alkyl, $R^3$ represents $C_1$-$C_6$-alkyl, $C_3$-$C_6$-cycloalkyl, 5- to 7-membered heterocyclyl, $C_6$-$C_{10}$-aryl, 5- or 6-membered heteroaryl, $C_1$-$C_6$-alkylcarbonyl, $C_1$-$C_6$-alkoxycarbonyl, $C_3$-$C_6$-cycloalkylcarbonyl, 5- to 7-membered heterocyclylcarbonyl, $C_6$-$C_{10}$-arylcarbonyl, 5- or 6-membered heteroarylcarbonyl or $C_1$-$C_6$-alkylaminocarbonyl, whereby alkyl, cycloalkyl, heterocyclyl, aryl, heteroaryl, alkoxycarbonyl, cycloalkylcarbonyl, heterocyclylcarbonyl, arylcarbonyl, heteroarylcarbonyl and alkylaminocarbonyl can be substituted with 0, 1, 2 or 3 substituents selected independently of one another from the group consisting of halogen, hydroxy, amino, $C_1$-$C_6$-alkylamino and phenyl, and whereby alkylcarbonyl is substituted with a substituent amino or $C_1$-$C_6$-alkylamino, and whereby alkylcarbonyl can be substituted with a further 0, 1 or 2 substituents selected independently of one another from the group consisting of halogen, hydroxy, trimethylsilyl, $C_1$-$C_6$-alkoxy, $C_1$-$C_6$-alkylthio, benzyloxy, $C_3$-$C_6$-cycloalkyl, phenyl, naphthyl, 5- to 10-membered heteroaryl, $C_1$-$C_6$-alkylcarbonlyamino, $C_1$-$C_6$-alkoxycarbonylamino, $C_6$-$C_{10}$-arylcarbonylamino, $C_6$-$C_{10}$-arylcarbonyloxy, benzyloxycarbonyl and benzyloxycarbonylamino, wherein phenyl and heteroaryl for their part can be substituted with 0, 1, 2 or 3 substituents selected independently of one another from the group consisting of halogen, hydroxy, nitro, $C_1$-$C_6$-alkyl, $C_1$-$C_6$-alkoxy and phenyl, $R^4$ represents hydrogen, $C_1$-$C_4$-alkyl, cyclopropyl or cyclopropylmethyl, and $R^5$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, $R^6$ represents hydrogen, $R^7$ represents hydrogen, or $R^5$ represents hydrogen, $R^6$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, $R^7$ represents hydrogen, or $R^5$ represents hydrogen, $R^6$ represents hydrogen, $R^7$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, or $R^5$ and $R^6$ are identical, and represent $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, $R^7$ represents hydrogen, and their salts, their solvates and the solvates of their salts.

Compounds of the invention are the compounds of formula (I) and their salts, solvates, solvates of the salts and prodrugs, the compounds of formulae mentioned below encompassed by formula (I) and their salts, solvates, solvates of the salts and prodrugs, and the compounds mentioned below as exemplary embodiments, encompassed by formula (I), and their salts, solvates, solvates of the salts and prodrugs, insofar as the compounds subsequently mentioned, encompassed by formula (I), are not already salts, solvates, solvates of the salts and prodrugs.

Depending on their structure, the compounds of the invention can exist in stereoisomeric forms (enantiomers, diastereomers). The invention therefore relates to the enantiomers or diastereomers and their respective mixtures. The stereoisomerically uniform constituents can be isolated in a known manner from such mixtures of enantiomers and/or diastereomers.

Where the compounds of the invention can occur in tautomeric forms, the present invention comprises all tautomeric forms.

Salts preferred for the purpose of the present invention are physiologically acceptable salts of the compounds of the invention. However, also included are salts which are themselves not suitable for pharmaceutical applications but can be used, for example, for the isolation or purification of the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases, such as, by way of example and preferably, alkali metal salts (e.g. sodium and potassium salts), alkaline earth metal salts (e.g. calcium and magnesium salts) and ammonium salts, derived from ammonia or organic amines having 1 to 16 C atoms, such as, by way of example and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purpose of the invention refer to those forms of the compounds of the invention which form a complex in the solid or liquid state by coordination with solvent molecules. Hydrates are a special form of solvates in which coordination takes place with water.

For the purposes the present invention, the substituents have the following meaning, unless specified otherwise:

Alkyl per se and "alk" and "alkyl" in alkoxy, alkylamino, alkylthio, alkylcarbonyl, alkoxycarbonyl, alkylaminocarbonyl, alkylaminosulfonyl, alkylcarbonylamino and alkoxycarbonylamino represents a linear or branched alkyl radical normally having 1 to 6, preferably 1 to 4, particularly preferably 1 to 3 carbon atoms, by way of example and preferably methyl, ethyl, n-propyl, isopropyl, tert-butyl, 2,2-dimethyl-prop-1-yl, n-pentyl and n-hexyl.

Alkoxy by way of example and preferably represents methoxy, ethoxy, n-propoxy, isopropoxy, tert-butoxy, n-pentoxy and n-hexoxy.

Alkylthio by way of example and preferably represents methylthio, ethylthio, n-propylthio, isopropylthio, tert-butylthio, n-pentylthio and n-hexylthio.

Alkenyl represents a straight-chain or branched alkenyl radical having 2 to 6 carbon atoms. A straight-chain or branched alkenyl radical having 2 to 4, particularly preferably having 2 to 3 carbon atoms, is preferred. For example and preferably, the following may be mentioned: vinyl, allyl, n-prop-1-en-1-yl, n-but-2-en-1-yl, 2-methylprop-1-en-1-yl and 2-methylprop-2-en-1-yl.

Alkylamino represents an alkylamino radical having one or two (chosen independently of one another) alkyl substituents, by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-Alkyl-amino, for example, represents a monoalkylamino radical having 1 to 3 carbon atoms or a dialkylamino radical having 1 to 3 carbon atoms each per alkyl substituent.

Arylamino represents an aryl substituent bonded via an amino group, with a further substituent optionally being bonded to the amino group, such as, for example, aryl or alkyl, by way of example and preferably phenylamino, naphthylamino, phenylmethylamino or diphenylamino.

Alkylcarbonyl represents, by way of example and preferably, methylcarbonyl, ethylcarbonyl, n-propylcarbonyl, isopropylcarbonyl, tert-butylcarbonyl, n-pentylcarbonyl and n-hexylcarbonyl.

Alkoxycarbonyl represents, by way of example and preferably, methoxycarbonyl, ethoxycarbonyl, n-propoxycarbonyl, isopropoxycarbonyl, tert-butoxycarbonyl, n-pentoxycarbonyl and n-hexoxycarbonyl.

Alkoxycarbonylamino represents, by way of example and preferably, methoxycarbonylamino, ethoxycarbonylamino, n-propoxycarbonylamino, isopropoxycarbonlyamino, tert-butoxycarbonylamino, n-pentoxycarbonylamino and n-hexoxycarbonylamino.

Cycloalkylcarbonyl represents a cycloalkyl substituent bonded via a carbonyl group, by way of example and preferably, cyclopropylcarbonyl, cyclobutylcarbonyl, cyclopentylcarbonyl and cyclohexylcarbonyl.

Heterocyclylcarbonyl represents a heterocyclyl substituent bonded via a carbonyl group, by way of example and preferably tetrahydrofuranylcarbonyl, pyrrolidinylcarbonyl, pyrrolinylcarbonyl, piperidinylcarbonyl, tetrahydropyranylcarbonyl, piperazinylcarbonyl, morpholinylcarbonyl and perhydroazepinylcarbonyl.

Arylcarbonyl represents an aryl substituent bonded via a carbonyl group, by way of example and preferably phenylcarbonyl, naphthylcarbonyl and phenanthrenylcarbonyl.

Heteroarylcarbonyl represents a heteroaryl substituent bonded via a carbonyl group, by way of example and preferably thienylcarbonyl, furylcarbonyl, pyrrolylcarbonyl, thiazolylcarbonyl, oxazolylcarbonyl, imidazolylcarbonyl, pyridylcarbonyl, pyrimidylcarbonyl, pyridazinylcarbonyl, indolylcarbonyl, indazolylcarbonyl, benzofuranylcarbonyl, benzothiophenylcarbonyl, quinolinylcarbonyl and isoquinolinylcarbonyl.

Alkylcarbonylamino represents, by way of example and preferably, methylcarbonylamino, ethylcarbonylamino, n-propylcarbonylamino, isopropylcarbonylamino, tert-butylcarbonylamino, n-pentylcarbonylamino and n-hexylcarbonylamino.

Arylcarbonylamino represents, by way of example and preferably, phenylcarbonylamino, naphthylcarbonylamino and phenanthrenylcarbonylamino.

Arylcarbonyloxy represents, by way of example and preferably, phenylcarbonyloxy, naphthylcarbonyloxy and phenanthrenylcarbonyloxy.

Alkylaminocarbonyl represents an alkylaminocarbonyl radical having one or two (chosen independently of one another) alkyl substituents, by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-N-methylaminocarbonyl. $C_1$-$C_3$-Alkylaminocarbonyl represents, for example, a monoalkylaminocarbonyl radical having 1 to 3 carbon atoms or a dialkylaminocarbonyl radical having 1 to 3 carbon atoms each per alkyl substituent.

Alkylaminosulfonyl represents an alkylaminosulfonyl radical having one or two (chosen independently of one another) alkyl substituents, by way of example and preferably methylaminosulfonyl, ethylaminosulfonyl, n-propylaminosulfonyl, isopropylaminosulfonyl, tert-butylaminosulfonyl, n-pentylaminosulfonyl, n-hexylaminosulfonyl, N,N-dimethylaminosulfonyl, N,N-diethylaminosulfonyl, N-ethyl-N-methylaminosulfonyl, N-methyl-N-n-propylaminosulfonyl, N-isopropyl-N-n-propylaminosulfonyl, N-tert-butyl-N-methylamino-sulfonyl, N-ethyl-N-n-pentylaminosulfonyl and N-n-hexyl-N-methylaminosulfonyl. $C_1$-$C_3$-Alkylaminosulfonyl represents, for example, a monoalkylaminosulfonyl radical having 1 to 3 carbon atoms or a dialkylaminosulfonyl radical having 1 to 3 carbon atoms each per alkyl substituent.

Arylaminocarbonyl represents an aryl substituent bonded via an aminocarbonyl group, with a further substituent such as, for example, aryl or alkyl, optionally being bonded to the aminocarbonyl group, by way of example and preferably phenylaminocarbonyl, naphthylaminocarbonyl, phenylmethylaminocarbonyl or diphenylaminocarbonyl.

Arylaminothiocarbonyl represents an aryl substituent bonded via an aminothiocarbonyl group, with a further substituent, such as, for example, aryl or alkyl, optionally being bonded to the aminothiocarbonyl group, by way of example and preferably phenylaminothiocarbonyl, naphthylaminothiocarbonyl, phenylmethylaminothiocarbonyl or diphenylaminothiocarbonyl.

Arylthiocarbonyl represents, by way of example and preferably, phenylthiocarbonyl, naphthylthiocarbonyl and phenanthrenylthiocarbonyl.

Arylsulfonylaminocarbonyl represents, by way of example and preferably, phenylsulfonylaminocarbonyl, naphthylsulfonylaminocarbonyl and phenanthrenylsulfonylaminocarbonyl.

Heteroarylaminocarbonyl represents a heteroaryl substituent bonded via an aminocarbonyl group, with a further substituent, such as, for example, aryl or alkyl, optionally being bonded to the aminocarbonyl group, by way of example and preferably thienylaminocarbonyl, furylaminocarbonyl, pyrrolylaminocarbonyl, thiazolylaminocarbonyl, oxazolylaminocarbonyl, imidazolylaminocarbonyl, pyridylaminocarbonyl, pyrimidylaminocarbonyl, pyridazinylaminocarbonyl, indolylaminocarbonyl, indazolylaminocarbonyl, benzofuranylaminocarbonyl, benzothiophenylaminocarbonyl, quinolinylaminocarbonyl, isoquinolinylaminocarbonyl, furylmethylaminocarbonyl and pyridylmethylaminocarbonyl.

Heteroarylaminothiocarbonyl represents a heteroaryl substituent bonded via an aminothiocarbonyl group, with a further substituent, such as, for example, aryl or alkyl, optionally being bonded to the aminothiocarbonyl group, by way of example and preferably thienylaminothiocarbonyl, furylaminothiocarbonyl, pyrrolylaminothiocarbonyl, thiazolylaminothiocarbonyl, oxazolylaminothiocarbonyl, imidazolylaminothiocarbonyl, pyridylaminothiocarbonyl, pyrimidylaminothiocarbonyl, pyridazinylaminothiocarbonyl, indolylaminothiocarbonyl, indazolylaminothiocarbonyl, benzofuranylaminothiocarbonyl, benzothiophenylaminothiocarbonyl, quinolinylaminothiocarbonyl, isoquinolinylaminothiocarbonyl, furylmethylaminothiocarbonyl and pyridylmethylaminothiocarbonyl.

Heteroarylthiocarbonyl represents a heteroaryl substituent bonded via a thiocarbonyl group, by way of example and preferably thienylthiocarbonyl, furylthiocarbonyl, pyrrolylthiocarbonyl, thiazolylthiocarbonyl, oxazolylthiocarbonyl, imidazolylthiocarbonyl, pyridylthiocarbonyl, pyrimidylthiocarbonyl, pyridazinylthiocarbonyl, indolylthiocarbonyl, indazolylthiocarbonyl, benzofuranylthiocarbonyl, benzothiophenylthiocarbonyl, quinolinylthiocarbonyl and isoquinolinylthiocarbonyl.

Cycloalkyl represents a cycloalkyl group normally having 3 to 6 carbon atoms, by way of example and preferably cyclopropyl, cyclobutyl, cyclopentyl and cyclohexyl.

Aryl represents a mono- to tricyclic aromatic, carbocyclic radical normally having 6 to 14 carbon atoms; by way of example and preferably phenyl, naphthyl and phenanthrenyl.

Heterocyclyl represents a mono- or polycyclic, preferably mono- or bicyclic, heterocyclic radical normally having 5 to 7 ring atoms and up to 3, preferably up to 2, heteroatoms and/or hetero groups from the series N, O, S, SO, $SO_2$. The heterocycyl radicals can be saturated or partly unsaturated. 5- to 7-membered, monocyclic saturated heterocyclyl radicals having up to two heteroatoms from the series O, N and S are preferred, such as, by way of example and preferably, tetrahydrofuran-2-yl, tetrahydrofuran-3-yl, pyrrolidin-2-yl, pyrrolidin-3-yl, pyrrolinyl, piperidin-1-yl, piperidin-2-yl, piperidin-3-yl, piperidin-4-yl, tetrahydropyran-2-yl, tetrahydropyran-3-yl, tetrahydropyran-4-yl, piperazin-1-yl, piperazin-2-yl, morpholin-2-yl, morpholin-3-yl, morpholin-4-yl, thiomorpholin-2-yl, thiomorpholin-3-yl, thiomorpholin-4-yl and perhydroazepinyl.

Heteroaryl represents an aromatic, mono- or bicyclic radical normally having 5 to 10, preferably 5 to 6 ring atoms and up to 5, preferably up to 4 heteroatoms from the series S, O and N, by way of example and preferably thien-2-yl, thien-3-yl, fur-2-yl, fur-3-yl, pyrrol-1-yl, pyrrol-2-yl, pyrrol-3-yl, thiazol-2-yl, thiazol-4-yl, thiazol-5-yl, oxazol-2-yl, oxazol-4-yl, oxazol-5-yl, imidazol-1-yl, imidazol-2-yl, imidazol-4-yl, imidazol-5-yl, pyrid-2-yl, pyrid-3-yl, pyrid-4-yl, pyrimid-2-yl, pyrimid-4-yl, pyrimid-5-yl, pyrazin-2-yl, pyrazin-3-yl, pyridazin-3-yl, pyridazin-4-yl, indolyl, indazolyl, benzofuranyl, benzothiophenyl, quinolinyl and isoquinolinyl.

Halogen represents fluorine, chlorine, bromine and iodine, preferably fluorine and chlorine.

Preferred compounds are those of formula (I) in which $R^1$ represents 2-methylprop-1-yl, 2,2-dimethylprop-1-yl, 2-pyridylmethyl or 3-pyridylmethyl, whereby 2-pyridylmethyl or 3-pyridylmethyl can be substituted with 0, 1, 2 or 3 substituents selected independently of one another from the group consisting of hydroxy, amino, trifluoromethyl, methyl, methoxy and morpholinyl, $R^2$ represents hydrogen, $R^3$ represents 1-amino-3-methylbut-1-ylcarbonyl, 1-amino-3,3-dimethylbut-1-ylcarbonyl or 1-amino-2-trimethylsilyleth-1-ylcarbonyl, $R^4$ represents hydrogen, and $R^5$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, $R^6$ represents hydrogen, $R^7$ represents hydrogen, or $R^5$ represents hydrogen, $R^6$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, $R^7$ represents hydrogen, or $R^5$ represents hydrogen, $R^6$ represents hydrogen, $R^7$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, or $R^5$ and $R^6$ are identical, and represent $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, $R^7$ represents hydrogen, and their salts, their solvates and the solvates of their salts.

Preferred compounds are also those of formula (I) in which $R^1$ represents 2-methylprop-1-yl, $R^2$ represents hydrogen, $R^3$ represents 1-amino-3-methylbut-1-ylcarbonyl, $R^4$ represents hydrogen, and $R^5$ represents hydrogen, $R^6$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, $R^7$ represents hydrogen, or $R^5$ represents hydrogen, $R^6$ represents hydrogen, $R^7$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylamino-sulfonyl, optionally oxo-substituted 5- to 7-membered heterocyclyl and 5- to 10-membered heteroaryl, and their salts, their solvates and the solvates of their salts.

Preferred compounds are also those of formula (I) in which $R^1$ represents 2-methylprop-1-yl, $R^2$ represents hydrogen, $R^3$ represents 1-amino-3-methylbut-1-ylcarbonyl, $R^4$ represents hydrogen, and $R^5$ represents hydrogen, $R^6$ represents phenylaminocarbonyl, phenylcarbonyl, pyridylaminocarbonyl or pyridylcarbonyl, whereby phenylaminocarbonyl, phenylcarbonyl, pyridylaminocarbonyl and pyridylcarbonyl can be substituted with 0, 1, 2 or 3 substituents selected independently of one another from the group consisting of pyrrolidinyl, piperidinyl, tetrahydropyranyl, piperazinyl, morpholinyl, 2-oxopyrrolidinyl and 2-oxopiperidinyl, $R^7$ represents hydrogen, or $R^5$ represents hydrogen, $R^6$ represents hydrogen, $R^7$ represents phenylaminocarbonyl, phenylcarbonyl, pyridylaminocarbonyl or pyridylcarbonyl, whereby phenylaminocarbonyl, phenylcarbonyl, pyridylaminocarbonyl and pyridylcarbonyl can be substituted with 0, 1, 2 or 3 substituents selected independently of one another from the group consisting of pyrrolidinyl, piperidinyl, tetrahydropyranyl, piperazinyl, morpholinyl, 2-oxopyrrolidinyl and 2-oxopiperidinyl, and their salts, their solvates and the solvates of their salts.

Preferred compounds are also those of formula (I) in which $R^1$ represents 2-methylprop-1-yl, $R^2$ represents hydrogen, $R^3$ represents 1-amino-3-methylbut-1-ylcarbonyl and $R^4$ represents hydrogen, and $R^5$, $R^6$ and $R^7$ have the meaning indicated above.

Preferred compounds are also those of formula (I) in which the stereocentre originating from an amino acid in $R^3$ has the D configuration.

Preferred compounds are also those of formula (I) in which $R^6$ and $R^7$ represent hydrogen and $R^5$ represent phenylaminocarbonyl, phenylcarbonyl, pyridylaminocarbonyl or pyridylcarbonyl, whereby phenylaminocarbonyl, phenylcarbonyl, pyridylaminocarbonyl and pyridylcarbonyl can be substituted with 0, 1, 2 or 3 substituents selected independently of one another from the group consisting of pyrrolidinyl, piperidinyl, tetrahydropyranyl, piperazinyl, morpholinyl, 2-oxopyrrolidinyl and 2-oxopiperidinyl, and $R^1$, $R^2$, $R^3$ and $R^4$ have the meaning indicated above.

Preferred compounds are also those of formula (I) in which $R^5$ and $R^7$ represent hydrogen and $R^6$ represents phenylaminocarbonyl, phenylcarbonyl, pyridylaminocarbonyl or pyridylcarbonyl, whereby phenylaminocarbonyl, phenylcarbonyl, pyridylaminocarbonyl and pyridylcarbonyl can be substituted with 0, 1, 2 or 3 substituents selected independently of one another from the group consisting of pyrrolidinyl, piperidinyl, tetrahydropyranyl, piperazinyl, morpholinyl, 2-oxopyrrolidinyl and 2-oxopiperidinyl, and $R^1$, $R^2$, $R^3$ and $R^4$ have the meaning indicated above.

Preferred compounds are also those of formula (I) in which $R^5$ and $R^6$ represent hydrogen and $R^7$ represents phenylaminocarbonyl, phenylcarbonyl, pyridylaminocarbonyl or pyridylcarbonyl, whereby phenylaminocarbonyl, phenylcarbonyl, pyridylaminocarbonyl and pyridylcarbonyl can be substituted with 0, 1, 2 or 3 substituents selected independently of one another from the group consisting of pyrrolidinyl, piperidinyl, tetrahydropyranyl, piperazinyl, morpholinyl, 2-oxopyrrolidinyl and 2-oxopiperidinyl, and $R^1$, $R^2$, $R^3$ and $R^4$ have the meaning indicated above.

The radical definitions indicated in detail in the respective combinations or preferred combinations of radicals are arbitrarily also replaced by radical definitions of different combination independently of the respective combinations of the radicals indicated.

Combinations of two or more of the abovementioned preferred ranges are also very particularly preferred.

The invention furthermore relates to a method for preparing the compounds of formula (I), whereby compounds of formula (II)

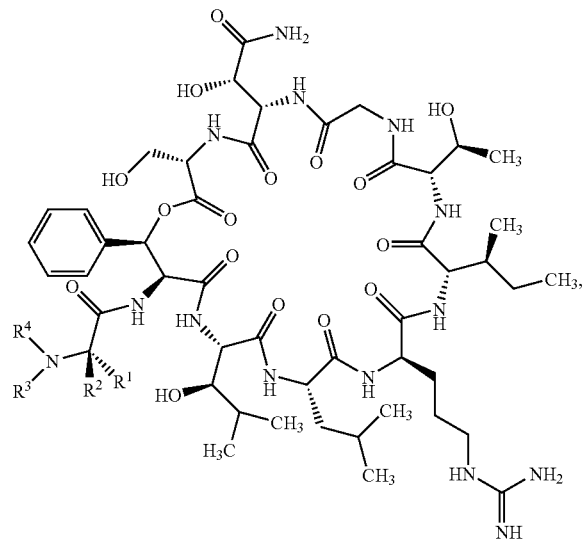

in which $R^1$, $R^2$, $R^3$ and $R^4$ have the meaning indicated above, are reacted with 1 to 10 equivalents, preferably 2 to 5 equivalents, of an aryl- or heteroarylcarbonyl chloride, of an aryl or heteroaryl isocyanate, of an aryl- or heteroarylthiocarbonyl chloride, of an aryl or heteroaryl isothiocyanate or of an arylsulfonyl isocyanate, whereby the aryl and heteroaryl radicals correspond to the aryl and heteroaryl radicals in the radicals $R^5$, $R^6$ and $R^7$, which have the meaning indicated above, and subsequently the resulting mixture of compounds of formula (I) is separated into the individual compounds of formula (I) by chromatography.

Free amino groups in the radicals $R^1$, $R^2$, $R^3$ and $R^4$ are protected before the reaction by the methods known to the person skilled in the art, for example using a Boc protecting group, which is removed again after the reaction and before chromatography.

The reaction with aryl- and heteroarylcarbonyl chlorides, aryl and heteroaryl isocyanates, aryl- and heteroarylthiocarbonyl chlorides, aryl and heteroaryl isothiocyanates and arylsulfonyl isocyanates is in general carried out in inert solvents, optionally in the presence of a base, preferably in a temperature range from −30° C. to 50° C. under atmospheric pressure.

Inert solvents are, for example, tetrahydrofuran, methylene chloride, pyridine, dioxane, dimethylformamide or a mixture of the solvents indicated. Preferred inert solvents are tetrahydrofuran, methylene chloride and dimethylformamide.

Bases are, for example, triethylamine, diisopropylethylamine or N-methylmorpholine; diisopropylethylamine is preferred.

The compounds of formula (I) which are present as salts can be converted into a salt having a different counter-ion, for example, by reaction with hydrochloric acid or methanesulfonic acid.

The aryl- and heteroarylcarbonyl chlorides, aryl and heteroaryl isocyanates, aryl- and heteroarylthiocarbonyl chlorides, aryl and heteroaryl isothiocyanates and arylsulfonyl isocyanates are known or can be prepared in analogy to known processes.

The compounds of formula (II) are known or can be prepared by reacting the compound of formula (III)

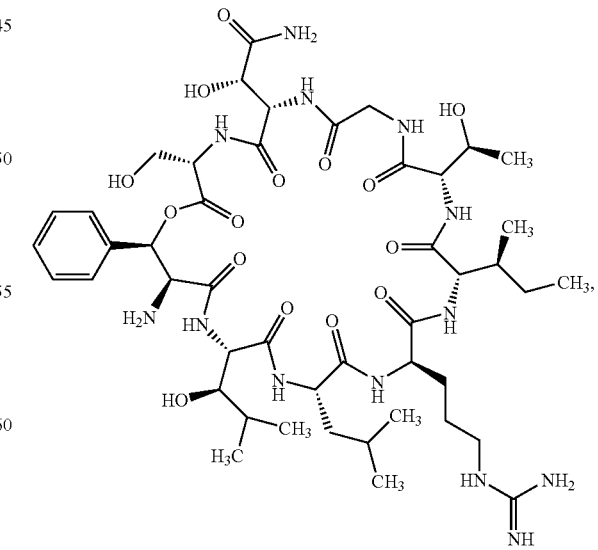

with compounds of formula

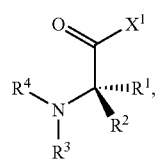

in which
R$^1$, R$^2$, R$^3$ and R$^4$ have the meaning indicated above, and
X$^1$ represents halogen, preferably bromine, chlorine or fluorine, or hydroxy.

If X$^1$ is halogen, the reaction generally takes place in inert solvents, where appropriate in the presence of a base, preferably in a temperature range from −30° C. to 50° C. under atmospheric pressure.

Inert solvents are, for example, tetrahydrofuran, methylene chloride, pyridine, dioxane or dimethylformamide. Preferred inert solvents are tetrahydrofuran or methylene chloride.

Bases are, for example, triethylamine, diisopropylethylamine or N-methylmorpholine; diisopropylethylamine is preferred.

If X$^1$ is hydroxy, the reaction generally takes place in inert solvents, in the presence of a dehydrating reagent, where appropriate in the presence of a base, preferably in a temperature range from −30° C. to 50° C. under atmospheric pressure.

Inert solvents are, for example, halohydrocarbons such as dichloromethane or trichloromethane, hydrocarbons such as benzene, nitromethane, dioxane, dimethylformamide or acetonitrile. It is likewise possible to employ mixtures of the solvents. Dichloromethane or dimethylformamide are particularly preferred.

Suitable dehydrating reagents hereby are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates, such as, for example, sodium or potassium carbonate, or hydrogencarbonate, or organic bases such as trialkylamines, e.g. triethylamine, N-methylmorpholine, N-methylpiperidine, 4-dimethylaminopyridine or diisopropyl ethyl amine.

Preferably, the condensation is carried out using HATU or using EDC in the presence of HOBt.

The compounds of formula (IV) optionally bear protecting groups, so that in these cases the reaction of the compound of formula (III) with compounds of formula (IV) is followed by the removal of the protecting groups using, for example, trifluoroacetic acid according to the methods known to the person skilled in the art.

The compound of formula (III) can be synthesized from lysobactin (Example 1A) by double Edmann degradation.

The compounds of formula (IV) are known or can be synthesized from the corresponding starting materials by known processes.

The preparation of the compounds of the invention can be illustrated by the following synthesis schemes.

Synthesis scheme:

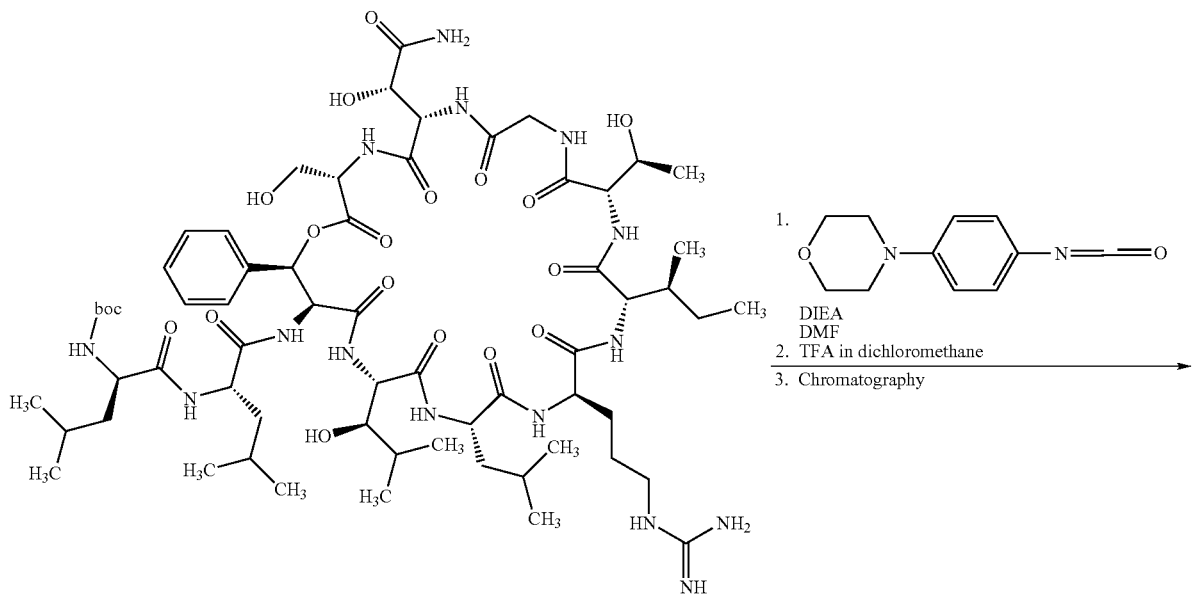

-continued
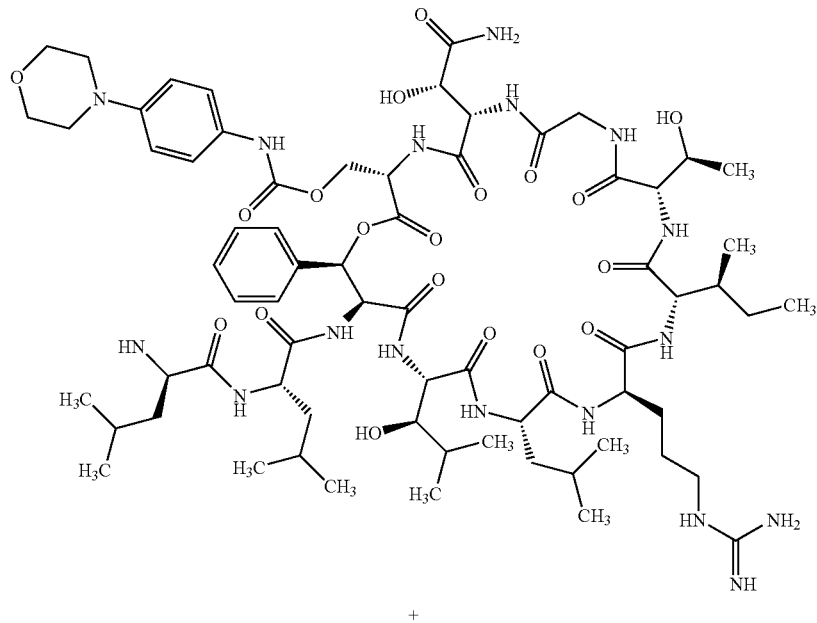
+
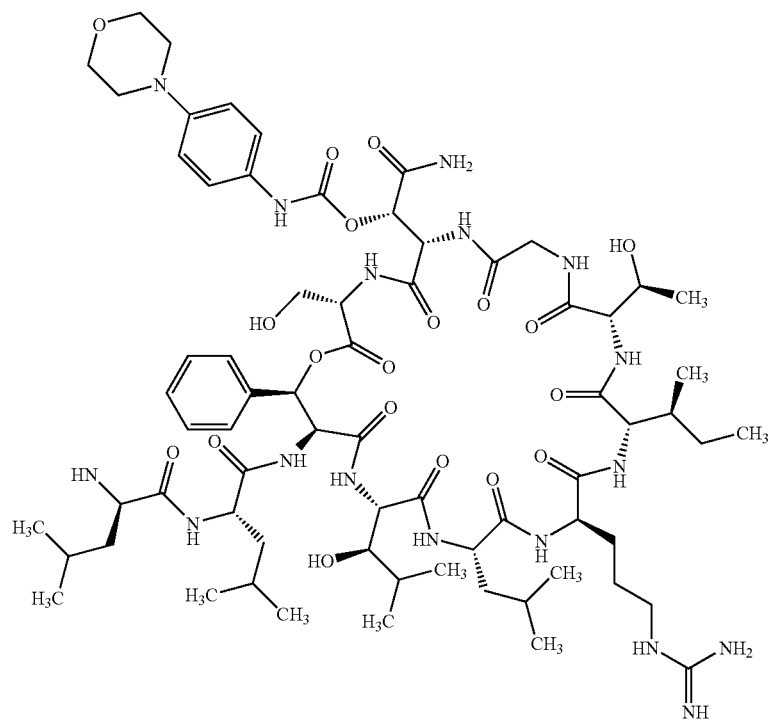
+

-continued

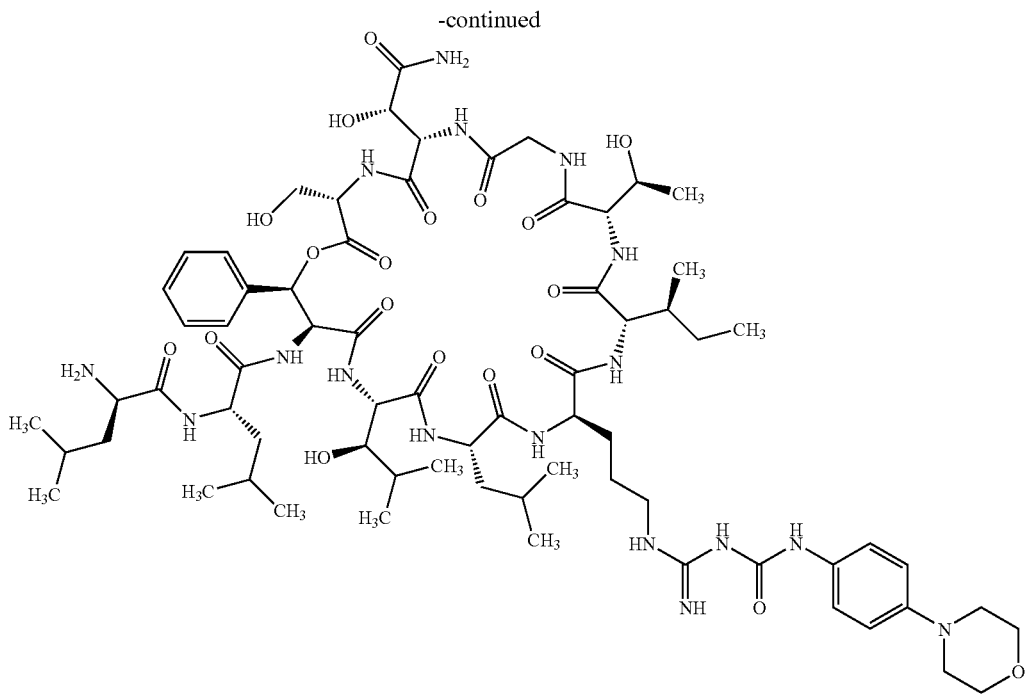

The compounds of the invention show a valuable spectrum of pharmacological activity which could not have been predicted. They show an antibacterial activity.

They are therefore suitable for use as medicaments for the treatment and/or prophylaxis of diseases in humans and animals.

The compounds of the invention are distinguished by a lower nephrotoxicity compared to lysobactin.

The compounds of the invention are distinguished by a better solubility compared to lysobactin.

The nonadepsipeptides described act as inhibitors of the bacterial cell wall biosynthesis.

The preparations of the invention are particularly effective against bacteria and bacteria-like microorganisms. They are therefore particularly suitable for the prophylaxis and chemotherapy of local and systemic infections in human and veterinary medicine which are caused by these pathogens.

In principle, the preparations of the invention can be used against all bacteria and bacteria-like microorganisms which possess a bacterial cell wall (Murein sacculus) or the corresponding enzyme systems, for example by the following pathogens or by mixtures of the following pathogens:

Gram-negative cocci (*Neisseria gonorrhoeae*) as well as Gram-negative rods such as Enterobacteriaceae, e.g. *Escherichia coli, Haemophilus influenzae, Pseudomonas, Klebsiella, Citrobacter* (*C. freundii, C. divernis*), *Salmonella* and *Shigella*; furthermore *Enterobacter* (*E. aerogenes, E. agglomerans*), *Hafnia, Serratia* (*S. marcescens*), *Providencia, Yersinia*, as well as the genus *Acinetobacter, Branhamella* and *Chlamydia*. Moreover, the antibacterial spectrum includes strictly anaerobic bacteria such as, for example, *Bacteroides fragilis*, representatives of the genus *Peptococcus, Peptostreptococcus* and the genus *Clostridium*; furthermore *Mycobacteria*, e.g. *M. tuberculosus*. The compounds of the invention show particularly a particularly pronounced effect on Gram-positive cocci, e.g. staphylococci (*S. aureus, S. epidermidis, S. haemolyticus, S. carnosus*), enterococci (*E. faecalis, E. faecium*) and streptococci (*S. agalactiae, S. pneumoniae, S. pyogenes*).

The above list of pathogens is to be interpreted only by way of example and in no way as restrictive. Diseases which may be mentioned which are caused by the pathogens mentioned or mixed infections and can be prevented, ameliorated or cured by the preparations of the invention are, for example:

Infectious diseases in humans such as, for example, uncomplicated and complicated urinary tract infections, uncomplicated skin and superficial infections, complicated skin and soft tissue infections, pneumonia acquired in hospital and as an outpatient, nosocomial pneumonia, acute exacerbations and secondary bacterial infections of chronic bronchitis, acute otitis media, acute sinusitis, streptococcal pharyngitis, bacterial meningitis, uncomplicated gonococcal and non-gonococcal urethritis/cervicitis, acute prostatitis, endocarditis, uncomplicated and complicated intra-abdominal infections, gynaecological infections, pelvic inflammatory disease, bacterial vaginosis, acute and chronic osteomyelitis, acute bacterial arthritis, empirical therapy in febrile neutropenic patients, furthermore bacteraemias, MRSA infections, acute infectious diarrhoea, *Helicobacter pylori* infections, postoperative infections, odontogenic infections, opthalmological infections, postoperative infections (including periproctal abscess, wound infections, biliary infections, mastitis and acute appendicitis), cystic fibrosis and bronchiectasis.

Apart from in humans, bacterial infections can also be treated in other species. Examples which may be mentioned are:

Pigs: diarrhoea, enterotoxaemia, sepsis, dysentery, salmonellosis, metritis-mastitis-agalactiae syndrome, mastitis;

Ruminants (cattle, sheep, goats): diarrhoea, sepsis, bronchopneumonia, salmonellosis, pasteurellosis, genital infections;

Horses: bronchopneumonia, joint-ill, puerperal and post-puerperal infections, salmonellosis;

Dogs and cats: bronchopneumonia, diarrhoea, dermatitis, otitis, urinary tract infections, prostatitis;

Poultry (chickens, turkeys, quails, pigeons, ornamental birds and others): *E. coli* infections, chronic respiratory diseases, salmonellosis, pasteurellosis, psittacosis.

It is likewise possible to treat bacterial diseases in the raising and keeping of productive and ornamental fish, the antibacterial spectrum thereby extending beyond the previously mentioned pathogens to further pathogens such as, for example, Pasteurella, Brucella, Campylobacter, Listeria, Erysipelothris, Corynebacteria, Borellia, Treponema, Nocardia, Rikettsia, Yersinia.

The present invention further relates to the use of the compounds of the invention for the treatment and/or prophylaxis of diseases, in particular of bacterial infectious diseases.

The present invention further relates to the use of the compounds of the invention for the treatment and/or prophylaxis of diseases, in particular the aforementioned diseases.

The present invention further relates to the use of the compounds of the invention for the production of a medicament for the treatment and/or prophylaxis of diseases, in particular the aforementioned diseases.

The compounds of the invention are preferably used for the production of medicaments which are suitable for the prophylaxis and/or treatment of bacterial diseases.

The present invention further relates to methods for the treatment and/or prophylaxis of diseases, in particular the aforementioned diseases, using an antibacterially effective amount of the compounds of the invention.

The present invention further relates to medicaments, comprising at least one compound of the invention and at least one or more further active compounds, in particular for the treatment and/or prophylaxis of the aforementioned diseases. Preferred active compounds for combination for combination are antibacterially active compounds which have a different spectrum of activity, in particular a supplementary spectrum of activity, and/or are synergistic to the compounds of the invention.

The compounds of the invention can act systemically and/or locally. For this purpose, they can be administered in a suitable way, such as, for example, orally, parenterally, pulmonarily, nasally, sublingually, lingually, buccally, rectally, dermally, transdermally, conjunctivally, otically or as an implant or stent.

The compounds of the invention can be administered in administration forms suitable for these routes of administration.

Suitable for oral administration, are administration forms which function according to the prior art and deliver the compounds of the invention rapidly and/or in a modified fashion and which contain the compounds of the invention in crystalline and/or amorphized and/or dissolved form, such as, for example, tablets (uncoated or coated tablets, for example having enteric coatings or coatings which are insoluble or dissolve with a delay and control the release of the compound of the invention), tablets or films/wafers, which disintegrate rapidly in the oral cavity, films/lyophilizates, capsules (for example hard or soft gelatine capsules), sugar-coated tablets, granules, pellets, powders, emulsions, suspensions, aerosols or solutions.

Parenteral administration can take place with avoidance of an absorption step (e.g. intravenous, intraarterial, intracardial, intraspinal or intralumbar) or with inclusion of an absorption (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates, or sterile powders.

Suitable for the other administration routes are, for example, pharmaceutical forms for inhalation (inter alia powder inhalers, nebulizers), nasal drops, solutions, sprays; tablets, films/wafers or capsules for lingual, sublingual or buccal administration, suppositories, preparations for ears or eyes, vaginal capsules, aqueous suspensions (lotions, shaking mixtures), lipophilic suspensions, ointments, creams, transdermal therapeutic systems (such as, for example, patches), milk, pastes, foams, dusting powder, implants or stents.

The compounds of the invention can be converted into the stated administration forms. This can take place in a manner known per se by mixing with inert, non-toxic, pharmaceutically acceptable excipients. These excipients include, inter alia, carriers (for example microcrystalline cellulose, lactose, mannitol), solvents (e.g. liquid polyethylene glycols), emulsifiers and dispersants or wetting agents (for example sodium dodecylsulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention furthermore relates to medicaments which comprise at least one compound of the invention, usually together with one or more inert, non-toxic, pharmaceutically acceptable excipients, and their use for the aforementioned purposes.

In general, it has proved advantageous on intravenous administration to administer amounts of about 0.001 to 100 mg/kg, preferably about 0.1 to 10 mg/kg of body weight to achieve effective results, and on oral administration the dosage is about 0.01 to 50 mg/kg, preferably 0.5 to 10 mg/kg, of body weight.

It may nevertheless be necessary where appropriate to deviate from the stated amounts, in particular as a function at body weight, route of administration, individual behaviour towards the active compound, type of preparation and time or interval over which administration takes place. Thus, in some cases it may be sufficient to make do with less than the aforementioned minimum amount, while in other cases the stated upper limit must be exceeded. In the case of the administration of larger amounts, it can be advisable to divide these into a number of individual doses over the course of the day.

The percentages in the following Tests and Examples are, unless indicated otherwise, percentages by weight; parts are parts by weight. Solvent ratios, dilution ratios and concentrations of liquid/liquid solutions are in each case based volume.

DETAILED DESCRIPTION OF PREFERRED EMBODIMENTS

A. Examples

| | Abbreviations |
|---|---|
| Area | (Peak) area |
| BHI | Brain heart infusion |
| Boc | tert-butyloxycarbonyl |
| br. | broad signal (in NMR spectra) |
| calc. | calculated |
| conc. | concentrated |
| D | doublet (in NMR spectra) |
| DCI | direct chemical ionization (in MS) |
| DCM | dichloromethane |
| DIEA | N,N-diisopropylethylamine |
| DMF | N,N-dimethylformamide |
| DMSO | dimethylsulfoxide |
| EA | ethyl acetate (acetic acid ethyl ester) |
| EDC | 1-ethyl-3-(3-dimethylaminopropyl)carbodiimide (also EDCI) |
| EDCxHCl | 1-ethyl-3-(3-dimethylaminopropyl)carbodiimide hydrochloride |
| EI | electron impact ionization (in MS) |
| ESI | electrospray ionization (in MS) |
| Ex. | Example |
| fnd. | found |
| Gen. | General |
| H | hour |
| HATU | O-(7-azabenzotriazol-1-yl)-N,N,N',N'-tetramethyluronium hexafluorophosphate |
| HOBt | 1-hydroxybenzotriazole |
| HPLC | high-pressure or high-performance liquid chromatography |
| HR | high resolution |
| i.V. | in vacuo |
| LC-MS | liquid chromatography-coupled mass spectroscopy |

-continued

| Abbreviations | |
|---|---|
| LDA | lithium diisopropylamide |
| m | middle (in UV and IR spectra) |
| m | multiplet (in NMR spectra) |
| MALDI | matrix-assisted laser desorption/ionization |
| MIC | minimum inhibitory concentration |
| min | minute/minutes |
| Mp. | melting point |
| MRSA | methicillin-resistant Staphylococcus aureus |
| MS | mass spectroscopy |
| NCCLS | National Committee for Clinical Laboratory Standards |
| neg. | negative |
| NMM | N-methylmorpholine |
| NMR | nuclear magnetic resonance spectroscopy |
| of th. | of theory |
| p.a. | per analysis |
| Pd-C | palladium on carbon |
| perc. | per cent |
| pos. | positive |
| quant. | quantitative |
| RP-HPLC | reverse phase HPLC |
| RT | room temperature |
| $R_t$ | retention time (in HPLC) |
| s | strong (in UV and IR spectra) |
| s | singlet (in NMR spectra) |
| satd. | saturated |
| TBTU | O-(benzotriazol-1-yl)-N,N,N',N'-tetramethyluronium tetrafluoroborate |
| TCTU | O-(1H-6-chlorobenzotriazol-1-yl)-1,1,3,3-tetramethyluronium tetrafluoroborate |
| TFA | trifluoroacetic acid |
| TFE | 2,2,2-trifluoroethanol |
| THF | tetrahydrofuran |
| TLC | thin-layer chromatography |
| TOF | time of flight |
| UV | ultraviolet |
| Vis | visible |
| VRSA | vancomycin-resisant Staphylococcus aureus |
| w | weak (in UV and IR spectra) |
| Z, Cbz | Benzyloxycarbonyl |

Literature

For the nomenclature of the peptides and cyclodepsipeptides cf.:

1. A Guide to IUPAC Nomenclature of Organic Compounds (Recommendations 1993), 1993, Blackwell Scientific publications.

2. Nomenclature and symbolism for amino acids and peptides. Recommendations 1983. IUPAC-IUB Joint Commission on Biochemical Nomenclature, UK. Biochemical Journal 1984, 219, 345-373. And cited literature.

3. For the nomenclature of nonadepsipeptide derivatives which are derivatized in the amino acid side chains, the IUPAC prefix system for the addressing of the respective derivatization site is used (IUPAC, Nomenclature and Symbolism for Amino Acids and Peptides, Names and Symbols for Derivatives of Named Peptides, Section 3AA-22, Recommendations 1983-1992). For instance, $N^{\omega.6}$-acetyllysobactin designates a lysobactin acetylated on amino acid 6 (calculated from the N-terminus of the depsipeptide, i.e. here D-Arg), especially on the terminal nitrogen atom. Analogously, $O^{3.11}$-methyllysobactin designates a derivative methylated on amino acid 11 (Ser) on the side chain oxygen atom ($O^3$).

General Methods LC-MS, HR-MS HPLC and Gel Chromatography

Method 1 (HPLC): instrument type HPLC: HP 1100 Series; UV DAD column: Zorbax Eclipse XBD-C8 (Agilent), 150 mm×4.6 mm, 5 μm; eluent A: 5 ml of $HClO_4$/l of water, eluent B: acetonitrile; gradient: O-1 min 10% B, 1-4 min 10-90% B, 4-5 min 90% B; flow: 2.0 ml/min; oven: 30° C.; UV detection: 210 and 254 nm.

Method 2 (HPLC): column: Kromasil RP-18, 60 mm×2 mm, 3.5 μm; eluent A: 5 ml of $HClO_4$/l of water, eluent B: acetonitrile; gradient: 0 min 2% B, 0.5 min 2% B, 4.5 min 90% B, 9 min 90% B; flow: 0.75 ml/min; oven: 30° C.; UV detection: 210 nm.

Method 3 (LC-MS): instrument type MS: Micromass ZQ; instrument type HPLC: HP 1100 Series; UV DAD; column: Phenomenex Synergi 2μ Hydro-RP Mercury 20 mm×4 mm; eluent A: 1l of water+0.5 ml of 50% formic acid, eluent B: 1l of acetonitrile+0.5 ml of 50% formic acid; gradient: 0.0 min 90% A→2.5 min 30% A→3.0 min 5% A→4.5 min 5% A; flow: 0.0 min, 1 ml/min, 2.5 min/3.0 min/4.5 min, 2 ml/min; oven: 50° C.; UV detection: 210 nm.

Method 4 (HPLC): column: Kromasil RP-18, 250 mm×4 mm, 5 μm; eluent A: 5 ml of $HClO_4$/l of water, eluent B: acetonitrile; gradient: 0 min 5% B, 10 min 95% B; flow: 1 ml/min; oven: 40° C.; UV detection: 210 nm.

Method 5 (HPLC): column: Kromasil RP-18, 250 mm×4 mm, 5 μm; eluent A: 2 ml of $HClO_4$/l of water, eluent B: acetonitrile; isocratic: 45% B, 55% A; flow: 1 ml/min; oven: 40° C.; UV detection: 210 nm.

Method 6 (HPLC): column: Kromasil RP-18, 250 mm×4 mm, 5 μm; eluent A: 2 ml of $HClO_4$/l of water, eluent B: acetonitrile; isocratic: 50% B, 50% A; flow: 1 ml/min; oven: 40° C.; UV detection: 210 nm.

Method 7 (MALDI-MS): The MALDI-MS/MS investigations are carried out using a 4700 Proteomics Analyzer (Applied Biosystems, Framingham, Mass., USA) which is equipped with TOF/TOF ion optics and a 200 Hz Nd:YAG laser (355 nm). The quasimolecular ions are accelerated in the ion source using 8 kV, selected using an electrical deflector (MS1), and impacted with argon atoms in an impact cell, which is arranged between MS1 and MS2. The resulting fragment ions are re-accelerated using 15 kV and characterized using the second time of flight mass analyser (MS2).

Method 8 (TOF-HR-MS): TOF-HR-MS-ESI+ Spectra are recorded using a Micromass LCT instrument (capillary voltage: 3.2 KV, cone voltage: 42 V, source temperature: 120° C., desolvation temperature: 280° C.). For this, a syringe pump (Harvard Apparatus) is used for the sample supply. Leucine encephalin (Tyr-Gly-Gly-Phe-Leu) (SEQ ID NO:1) is used as standard.

Method 9 (Sephadex LH-20 gel chromatography): Gel chromatography is carried out without pressure on Sephadex LH-20 (Pharmacia). Fractionation (ISCO Foxy 200 fraction collector) is carried out according to UV activity (UV detector for 210 nm, Knauer). Column dimensions: 60×21 cm (2500-5000 μmol scale); 50×10 cm (500-2500 μmol scale); 30×5 cm (250-500 μmol scale); 25×4 cm (50-250 μmol scale); 40×2 cm (5-50 μmol scale).

Method 10 (Reprosil): column: Gilson Abimed HPLC; Varian binary pump system; Reprosil ODS-A 5μ 250 mm×20 mm; flow: 25 ml/min; oven: RT; UV detection: 210 nm; eluent A: water/0.2% TFA, eluent B: acetonitrile; gradient: 0-10 min 5-95% B, subsequent regeneration of the chromatography column.

Method 11 (Reprosil): column: Gilson Abimed HPLC; Varian binary pump system; Reprosil ODS-A 5μ 250 mm×20 mm; flow: 25 ml/min; oven: RT; UV detection: 210 nm; eluent A: water/0.2% TFA, eluent B: acetonitrile; gradient: 0-10 min 15-65% B, subsequent regeneration of the chromatography column.

Method 12 (Phenomenex Luna): column: Gilson Abimed HPLC; Varian binary pump system; Phenomenex Luna C18 5μ 250 mm×20 mm; flow: 25 ml/min; oven: RT; UV detection: 210 nm; eluent A: water/0.2% TFA, eluent B: acetonitrile; isocratic 50% B.

Method 13 (Kromasil): column: Gilson Abimed HPLC; Varian binary pump system; Kromasil 100 C18 5μ 250 mm×20 mm; flow: 25 ml/min; oven: RT; UV detection: 210 nm; eluent A: water/0.2% TFA, eluent B: acetonitrile; isocratic 65% B.

Method 14 (Reprosil): column: Gilson Abimed HPLC; Varian binary pump system; Reprosil ODS-A 5μ 250 mm×20 mm; flow: 25 ml/min; oven: RT; UV detection: 210 nm; eluent A: water/0.2% TFA, eluent B: acetonitrile; gradient: 0-15 min 10-90% B, subsequent regeneration of the chromatography column.

Method 15 (Kromasil): column: Gilson Abimed HPLC; Varian binary pump system; Kromasil 100 C18 5μ 250 mm×20 mm; flow: 25 ml/min; oven: 40° C.; UV detection: 210 nm; eluent A: water/0.2% TFA, eluent B: acetonitrile; gradient: 0-15 min 70-55% A, 15.1-20 min 70% A, subsequent regeneration of the chromatography column Method 16 (Reprosil): column: Gilson Abimed HPLC; Varian binary pump system; Reprosil ODS-A 5μ 250 mm×20 mm; flow: 25 ml/min; oven: RT; UV detection: 210 nm; eluent A: water/0.2% TFA, eluent B: acetonitrile; isocratic 57% A.

Method 17 (Symmetryprep): instrument: Gilson Abimed HPLC; UV detector 210 nm; binary pump system; column: SymmetryPrep™ $C_{18}$, Waters, 7 μm; 300 mm×19 mm; flow: 7 ml/min; eluent A: water/0.5% TFA, eluent B: acetonitrile/0.5% TFA; gradient: 0-5 min 5% B, 5-30 min 5-60% B, 30-35 min 60-98% B, 35-40 min 98% B, subsequent regeneration of the chromatography column.

Method 18 (cHPLC-MALDI-MS): The MALDI-MS/MS investigations are carried out using a 4700 Proteomics Analyzer (Applied Biosystems, Framingham, Mass., USA) which is equipped with TOF/TOF ion optics and a 200 Hz Nd:YAG laser (355 nm). The quasimolecular ions are accelerated in the ion source using 8 kV, selected using an electrical deflector (MS1), and impacted with argon atoms in an impact cell which is arranged between MS1 and MS2. The resulting fragment ions are re-accelerated using 15 kV and characterized using the second time of flight mass analyser (MS2). The cHPLC-MALDI-TOF/TOF coupling is carried out offline by means of a PROBOT system (Dionex).

General Working Procedures

General Working Procedure 1 (Esterification)

DIEA (1 mmol) and an acid chloride (0.3 mmol) are added under an argon protective gas atmosphere to a solution of the N-Boc protected peptide (0.3 mmol) in dry DCM (10 ml). The reaction mixture is stirred at RT. The course of the reaction is checked by means of analytical HPLC (Method 13). Further portions of acid chloride (0.3 mmol each) are added until the analytical HPLC indicates adequate conversion (>95%). The reaction mixture is treated with acetic acid (pH about 7) and then purified by chromatography using Method 9 (methanol/acetone: 4/1, 0.5% acetic acid) and/or Method 12.

General Working Procedure 2 (Carbamoylation)

DIEA (1 mmol) and an isocyanate (0.3 mmol) are added under an argon protective gas atmosphere to a solution of the N-Boc protected peptide (0.3 mmol) in dry DMF (100 ml). The reaction mixture is stirred at RT. The course of the reaction is checked by means of analytical HPLC (Method 13). Further portions of isocyanate (0.3 mmol each) are added until the analytical HPLC indicates adequate conversion (>95%). The reaction mixture is treated with acetic acid (pH about 7) and then purified by chromatography using Method 9 (methanol/acetone: 4/1, 0.5% acetic acid) and/or Method 12.

General Working Procedure 3 (Hydrolytic Sample Preparation for MALDI-MS)

The depsipeptide to be opened (e.g. lysobactin, 0.05 μmol) is first treated with a borate-hydrochloric acid buffer (Merck) pH 8 (250 μl) in a microvial (500 μl to 1000 μl). The mixture is allowed to stand overnight, acetic acid (100 μl) is added and the sample is freeze-dried. The crude product is investigated steps by means of MALDI-MS sequencing without further purification.

Starting Compounds

Example 1A

D-Leucyl-$N^1$-{(3S,6S,12S,15S,18R,21S,24S,27S,28R)-6-[(1S)-2-amino-1-hydroxy-2-oxoethyl]-18-(3-{[amino(imino)methyl]amino}propyl)-12-[(1S)-1-hydroxyethyl]-3-(hydroxymethyl)-24-[(1R)-1-hydroxy-2-methylpropyl]-21-isobutyl-15-[(1S)-1-methylpropyl]-2,5,8,11,14,17,20,23,26-nonaoxo-28-phenyl-1-oxa-4,7,10,13,16,19,22,25-octaazacyclooctacosan-27-yl}-L-leucinamide bistrifluoroacetate (lysobactin)

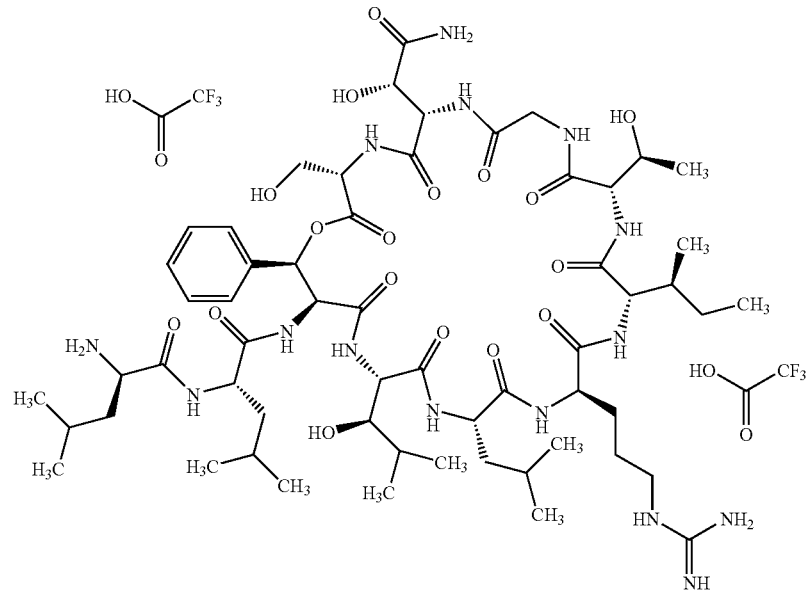

Fermentation:
Culture Medium:
YM: yeast-malt agar: D-glucose (4 g/l), yeast extract (4 g/l), malt extract (10 g/l), 1 litre of Lewatit water. Before sterilization (20 minutes at 121° C.), the pH is adjusted to 7.2.
HPM: mannitol (5.4 g/l), yeast extract (5 g/l), meat peptone (3 g/l).

Working preserve: The lyophilized strain (ATCC 53042) is grown in 50 ml of YM medium.

Flask fermentation: 150 ml of YM medium or 100 ml of HPM medium in a 1 l Erlenmeyer flask are inoculated with 2 ml of the working preserve and allowed to grow at 28° C. on a shaker at 240 rpm for 30-48 hours.

30 l fermentation: 300 ml of the flask fermentation (HPM medium) are used to inoculate a sterile 30 l nutrient medium solution (1 ml of antifoam SAG 5693/1). This culture is allowed to grow for 21 hours at 28° C., 300 rpm and aeration with sterile air of 0.3 vvm. The pH is kept constant at pH=7.2 with 1 M hydrochloric acid. In total, 880 ml of 1 M hydrochloric acid are added during the culturing period.

Main culture (200 l): 15×150 ml of YM medium in 1 l Erlenmeyer flasks are inoculated with 2 ml of the working preserve and allowed to grow on the shaker for 48 hours at 28° C. and 240 rpm. 2250 ml of this culture are used to inoculate a sterile 200 l nutrient medium solution (YM) (1 ml of antifoam SAG 5693/l) and it is allowed to grow for 18.5 hours at 28° C., 150 rpm and aeration with sterile air of 0.3 vvm.

Hourly samples (50 ml) are taken to check the course of the fermentation. 1 ml of methanol (0.5% trifluoroacetic acid) is added to 2 ml of this culture broth and the mixture filtered through a 0.45 μm filter. 30 l of this suspension are analysed by means of HPLC (Method 1 and Method 2).

After 18.5 hours, the culture broth of the main culture is separated into supernatant and sediment at 17 000 rpm.

Isolation:
The supernatant (183 l) is adjusted to pH 6.5-7 using concentrated trifluoroacetic acid or a sodium hydroxide solution and loaded onto a Lewapol column (OC 1064, 60 l contents). Elution is subsequently carried out with pure water, water/methanol 1:1 and subsequently with pure methanol (containing 0.1% trifluoroacetic acid). This organic phase is concentrated in vacuo to a residual aqueous residue of 11.5 l.

The residual aqueous phase is bound to silica gel $C_{18}$ and separated (MPLC, Biotage Flash 75, 75×30 cm, KP-C18-WP, 15-20 μm, flow: 30 ml; eluent: acetonitrile/water containing 0.1% trifluoroacetic acid; gradient: 10%, 15% and 40% acetonitrile). The 40% acetonitrile phase, which contains the main amount of Example 1A, is concentrated in vacuo and subsequently lyophilized (about 13 g). This mixture of solids is separated in 1.2 g portions, first on a preparative HPLC (Method 3), subsequently by gel filtration on Sephadex LH-20 (5×70 cm, acetonitrile/water 1:1, in each case containing 0.05% trifluoroacetic acid) and a further preparative HPLC (Method 4).

This process yields 2250 mg of Example 1A.

The sediment is taken up in 4 l of acetone/water 4:1, 2 kg of Celite are added, the mixture is adjusted to pH=6 using trifluoroacetic acid, stirred and centrifuged. The solvent is concentrated in vacuo and the residue is freeze-dried. The lyophilizate obtained (89.9 g) is taken up in methanol, filtered, concentrated and separated on silica gel (Method 5). Example 1A is then purified by gel filtration (Sephadex LH-20, 5×68 cm, water/acetonitrile 9:1 (containing 0.05% trifluoroacetic acid), flow: 2.7 ml/min, fraction size 13.5 ml) to give the pure substance.

This process yields 447 mg of Example 1A.

HPLC (Method 1): $R_t$=6.19 min

MS (ESIpos): m/z=1277 (M+H)+

$^1$H NMR (500.13 MHz, $d_6$-DMSO): δ=0.75 (d, 3H), 0.78 (d, 6H), 0.80 (t, 3H), 0.82 (d, 3H), 0.90 (d, 3H), 0.91 (d, 3H), 0.92 (d, 3H), 0.95 (d, 3H), 0.96 (d, 3H), 1.05 (m, 1H), 1.19 (d, 3H), 1.25 (m, 2H), 1.50 (m, 4H), 1.51 (m, 2H), 1.55 (m, 1H), 1.61 (m, 1H), 1.65 (m, 1H), 1.84 (m, 1H), 1.85 (m, 1H), 1.86 (m, 1H), 1.89 (m, 1H), 1.95 (m, 1H), 2.75 (m, 2H), 3.40 (m, 1H), 3.52 (m, 2H), 3.53 (dd, 1H), 3.64 (m, 2H), 3.66 (m, 1H), 3.68 (dd, 1H), 3.73 (m, 2H), 4.00 (dd, 1H), 4.02 (br., 1H), 4.13 (br., 1H), 4.32 (dd, 1H), 4.39 (t, 1H), 4.55 (m, 1H), 4.75 (dd, 1H), 5.19 (t, 1H), 5.29 (d, 1H), 5.30 (br., 1H), 5.58 (m, 2H), 6.68 (m, 3H), 6.89 (d, 1H), 6.93 (m, 3H), 6.94 (br., 1H), 6.98 (d, 1H), 7.12 (br., 1H), 7.20 (br., 2H), 7.23 (m, 2H), 7.42 (m, 2H), 7.54 (d, 1H), 7.58 (d, 1H), 8.32 (br., 1H), 9.18 (br., 1H), 9.20 (m, 2H), 9.50 (br., 1H).

$^{13}$C-NMR (125.77 MHz, $d_6$-DMSO): δ=10.3, 15.3, 19.0, 19.2, 19.6, 20.0, 20.9, 22.0, 22.4, 23.0, 23.2, 24.3, 24.4, 25.0, 25.4, 26.0, 27.8, 30.9, 35.4, 39.5, 40.8, 40.9, 41.6, 44.1, 51.5, 52.7, 55.9, 56.2, 56.4, 57.9, 58.8, 60.2, 61.1, 62.6, 70.1, 71.6, 71.7, 75.5, 128.1, 128.6, 136.7, 156.8, 168.2, 170.1, 170.4, 171.2, 171.5, 171.9, 172.2, 172.4, 173.7.

The assignment of the signals was carried out according to the assignment described in the literature (T. Kato, H. Hinoo, Y. Terui, *J. Antibiot.*, 1988, 61, 719-725).

Example 2A

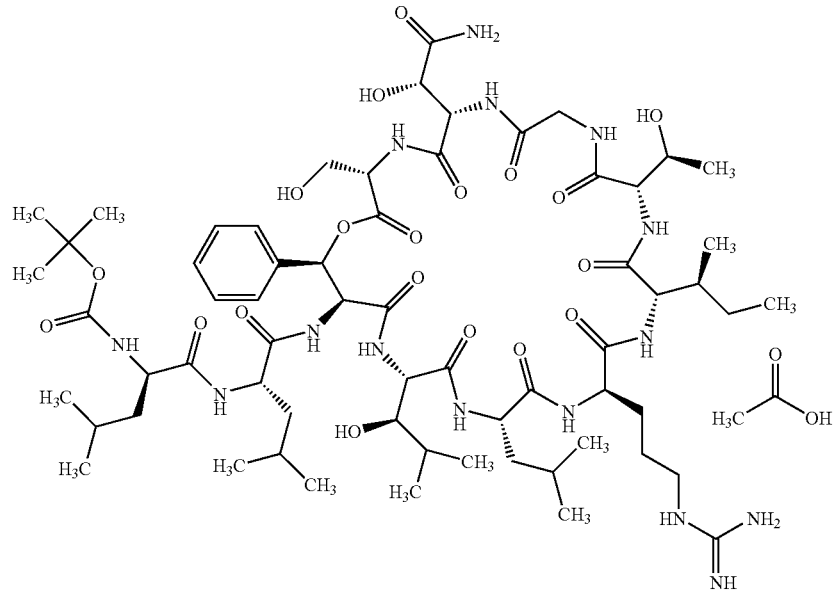

$N^1$-tert-Butoxycarbonyllysobactin acetate 10.0 g (5.18 mmol; 78%) of lysobactin (Example 1A) are dissolved in 2 l of a mixture of tert-butanol/buffer solution (pH6)/buffer solution (pH7) (2:1:1). First, 6.7 mmol (1.2 equivalents) of di-tert-butyl dicarbonate in 5 ml of tert-butanol/buffer mixture and subsequently 6.7 mmol (1.2 equivalents) of DIEA in 5 ml of tert-butanol/buffer mixture are added dropwise at 20° C. After 12 hours, no complete conversion is observed by means of analytical HPLC (Method 1). A further 6.7 mmol (1.2 equivalents) of di-tert-butyl dicarbonate in 5 ml of tert-butanol/buffer mixture are added dropwise. After one hour the reaction is complete, whereupon 2.58 ml (45 mmol) of acetic acid are added. The crude product is concentrated, lyophilized and coarsely purified by gel chromatography (Method 9; methanol:acetone:acetic acid/80:20:0.1) and finely purified by means of preparative HPLC (Method 10). 5.76 g (74% of th.) of product are obtained.

$[\alpha]^{20}_{Na}=-56°$ (c=0.21 in methanol).

HPLC/UV-vis (Method 2): $R_t$=4.7 min.

HPLC (Method 1): $R_t$=4.29 min

LC-MS (Method 3): $R_t$=2.02 min;

MS (ESIpos.): m/z (%)=639 (100), 1376 (40) [M-CO$_2$—C$_4$H$_8$+H]$^+$

MS (ESIneg.): m/z (%)=687 (100), 1374 (5) [M-CO$_2$—C$_4$H$_8$-H]$^-$.

HR-TOF-MS (Method 8): C$_{63}$H$_{106}$N$_{15}$O$_{19}$ calc. 1376.7789, fnd. 1376.7820;

Exemplary Embodiments

Examples 1 to 3

250 mg (0.17 mmol) of Example 2A are reacted according to General working procedure 2. After the reaction with phenyl isocyanate, 105 mg of a mixture of several monosubstituted Boc-protected lysobactin derivatives are isolated.

HPLC (Method 2): $R_t$=4.54 min; $\lambda_{max}$ (qualitative)=208 nm (s), 234 nm (m);

LC-MS (Method 3): $R_t$=2.47 min;

MS (ESIpos.): m/z (%)=698 (100) [M-CO$_2$—C$_4$H$_8$+2H]$^{2+}$, 748 (5) [M+2H]$^{2+}$, 1495 (100) [M+H]$^+$;

MS (ESIneg.): m/z (%)=687 (80), 1493 (100) [M-H]$^-$.

The mixture is provided as a suspension in 3 ml of DCM, 1 ml of TFA is added and the mixture is stirred at RT for 15 min, until the analytical HPLC (Method 1) indicates complete conversion. The crude product is freed of solvent in vacuo. Finally, the crude product is coarsely purified by gel chromatography (Method 9; methanol:acetone:TFA/80:20:0.1) and finely purified and separated by means of preparative HPLC (Method 11). 41.4 mg (17% of th.) of Example 1, 30.1 mg (25% of th.) of Example 2 and 5.8 mg (3% of th.) of Example 3 are obtained.

Example 1

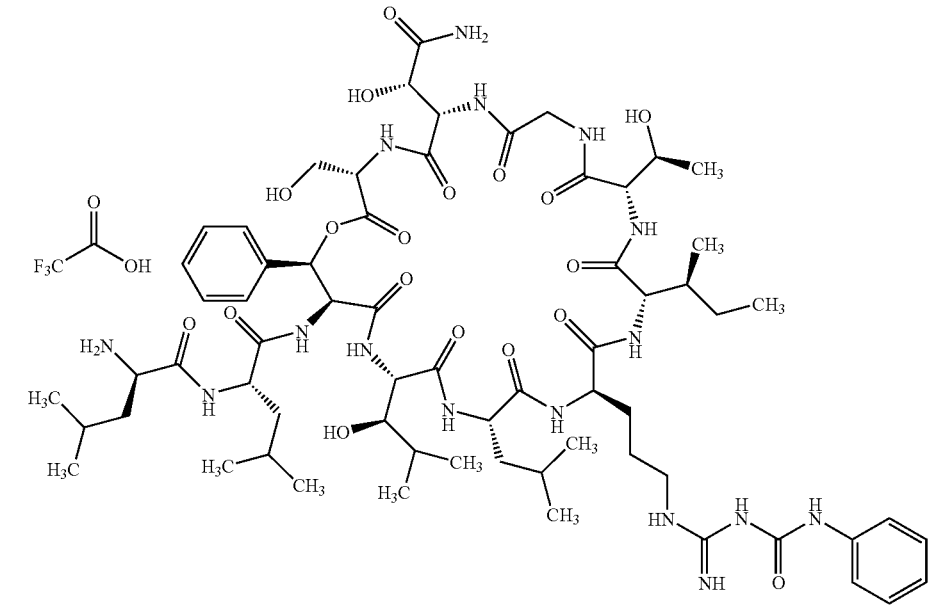

N$^{\omega,6}$-(Phenylaminocarbonyl)lysobactin trifluoroacetate

HPLC/UV-vis (Method 2): $R_t$=4.1 min.

$\lambda_{max}$ (qualitative)=220 nm (s), 240 nm (m).

HPLC (Method 1): $R_t$=3.70 min

HPLC (Method 4): $R_t$=8.36 min

LC-MS (Method 3): $R_t$=1.52 min;

MS (ESIpos.): m/z (%)=698 (100) [M+2H]$^{2+}$, 1395 (5) [M+H]$^+$

MS (ESIneg.): m/z (%)=696 (100), 1393 (30) [M-H]$^-$.

HR-TOF-MS (Method 8): C$_{65}$H$_{103}$N$_{16}$O$_{18}$ (MH$^+$) calc. 1395.7636, fnd. 1395.7604;

For the amino acid sequence determination, an analytical sample of the product is hydrolysed according to General working procedure 3 and analysed (Method 7).

Example 2

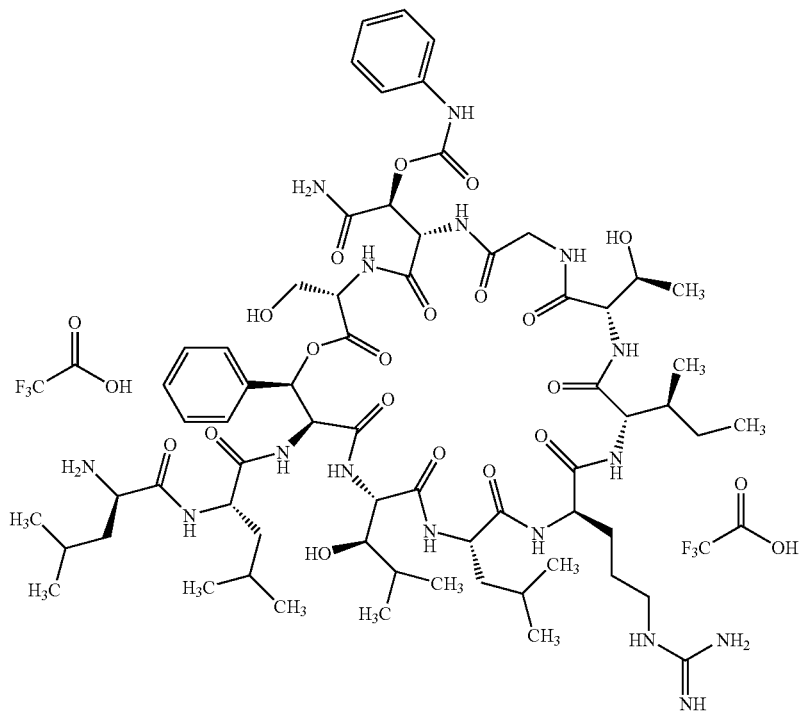

O$^{3.10}$-(Phenylaminocarbonyl)lysobactin bistrifluoroacetate

HPLC/UV-vis (Method 1): $R_t$=4.1 min.
$\lambda_{max}$ (qualitative)=242 nm (m).
HPLC (Method 2): $R_t$=3.70 min
HPLC (Method 4): $R_t$=8.70 min
LC-MS (Method 3): $R_t$=1.60 min;
MS (ESIpos.): m/z (%)=698 (100) [M+2H]$^{2+}$, 1395 (5) [M+H]$^+$ MS (ESIneg.): m/z (%)=636 (100), 1393 (5) [M–H]$^-$.
HR-TOF-MS (Method 8): $C_{65}H_{103}N_{16}O_{18}$ (MH$^+$) calc. 1395.7636, fnd. 1395.7653;

For the amino acid sequence determination, an analytical sample of the product is hydrolysed according to General working procedure 3 and analysed (Method 7).

Example 3

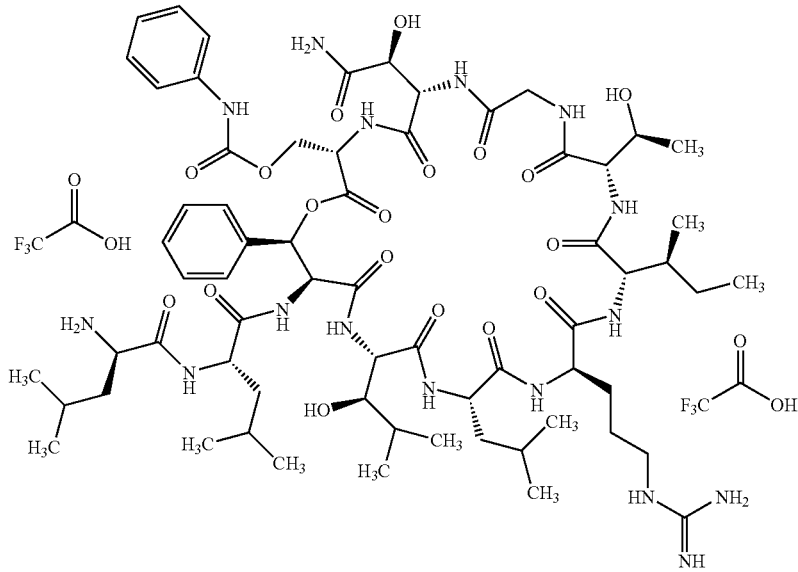

O$^{3.11}$-(Phenylaminocarbonyl)lysobactin bistrifluoroacetate

HPLC/IUV-vis (Method 1): $R_t$=4.3 min.
$\lambda_{max}$ (qualitative)=232 nm (m).
HPLC (Method 2): $R_t$=3.79 min
HPLC (Method 4): $R_t$=8.89 min
LC-MS (Method 3): $R_t$=1.72 min;
MS (ESIpos.): m/z (%)=698 (100) $[M+2H]^{2+}$, 1395 (5) $[M+H]^+$
MS (ESIneg.): m/z (%)=136 (10), 637 (60), 696 (30), 1393 (30) $[M-H]^-$.
HR-TOF-MS (Method 8): $C_{65}H_{103}N_{16}O_{18}$ $(MH^+)$ calc. 1395.7636, fnd. 1395.7639;

For the amino acid sequence determination, an analytical sample of the product is hydrolysed according to General working procedure 3 and analysed (Method 7).

Examples 4 to 6

500 mg (0.35 mmol) of Example 2A are reacted according to General working procedure 2. After the reaction with 3-methoxyphenyl isocyanate, 125.7 mg of a mixture of several mono-substituted derivatives of Example 2A are isolated.
HPLC (Method 1): $R_t$=4.55 min;
LC-MS (Method 3): $R_t$=2.21 min;
MS (ESIpos.): m/z (%)=713 (100) $[M-Boc+2H]^{2+}$, 763 (5) $[M+2H]^{2+}$, 1525 (60) $[M+H]^+$;
MS (ESIneg.): m/z (%) 761 (100), 1523 (15) $[M-H]^-$).

The mixture is provided as a suspension in 4.5 ml of DCM, 1.5 ml of TFA are added and the mixture is stirred at RT for 10 min, until complete conversion is indicated by analytical HPLC (Method 1). The crude product is freed of solvent in vacuo. Finally, the crude product is coarsely purified by gel chromatography (Method 9; methanol:acetone:TFA/80:20: 0.1) and finely purified and separated by means of preparative HPLC (Method 13). 30.5 mg (5% of th.) of Example 4, 30.5 mg (5% of th.) of Example 5 and 30.5 mg (4% of th.) of Example 6 are obtained.

Example 4

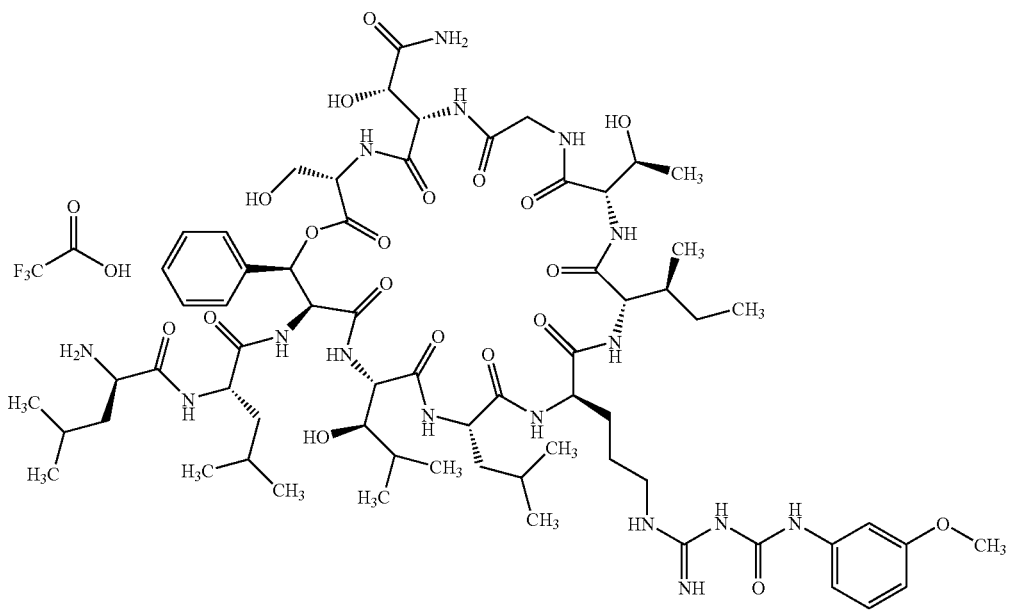

$N^{\omega,6}$-(3-Methoxyphenylaminocarbonyl)lysobactin trifluoroacetate

HPLC/UV-vis (Method 2): $R_t$=4.1 min.
$\lambda_{max}$ (qualitative)=210 nm (m), 245 nm (w).
HPLC (Method 5): $R_t$=4.88 min.
LC-MS (Method 3): $R_t$=1.56 min;
MS (ESIpos.): m/z (%)=713 (100) $[M+2H]^{2+}$, 1425 (10) $[M+H]^+$
MS (ESIneg.): m/z (%)=711 (100), 1423 (20) $[M-H]^-$.
HR-TOF-MS (Method 8): $C_{66}H_{105}N_{16}O_{19}$ $(MH^+)$ calc. 1425.7742, fnd. 1425.7766;

For the amino acid sequence determination, an analytical sample of the product is hydrolysed according to General working procedure 3 and analysed (Method 7).

Example 5

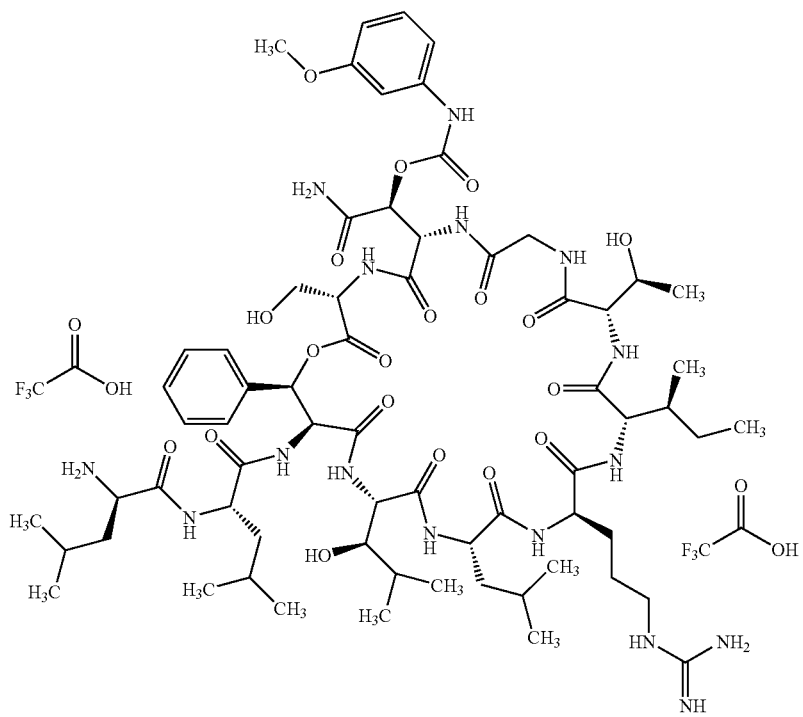

$O^{3.10}$-(3-Methoxyphenylaminocarbonyl)lysobactin bistrifluoroacetate

HPLC/UV-vis (Method 2): $R_t$=4.2 min.
$\lambda_{max}$ (qualitative)-210 nm (m), 245 nm (w).
HPLC (Method 5): $R_t$=6.71 min.
LC-MS (Method 3): $R_t$=1.67 min;
MS (ESIpos.): m/z (%)=713 (100) [M+2H]$^{2+}$, 1425 (10) [M+H]$^+$ HR-TOF-MS (Method 8): $C_{66}H_{105}N_{16}O_{19}$ (MH$^+$) calc. 1425.7742, fnd. 1425.7761;

For the amino acid sequence determination, an analytical sample of the product is hydrolysed according to General working procedure 3 and analysed (Method 7).

Example 6

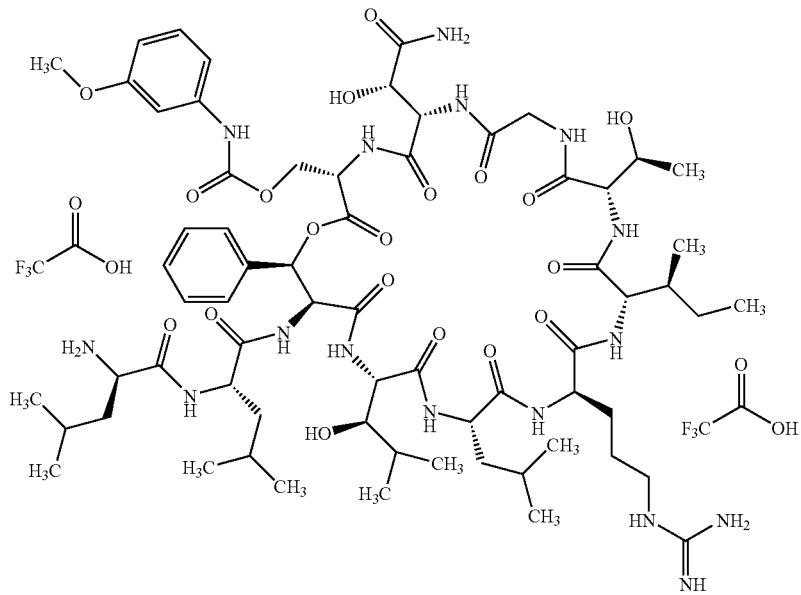

$O^{3.11}$-(3-Methoxyphenylaminocarbonyl)lysobactin bistrifluoroacetate

HPLC/UV-vis (Method 2): $R_t$=4.3 min.
$\lambda_{max}$ (qualitative)=210 nm (m), 245 nm (w).
HPLC (Method 5): $R_t$=8.21 min.
LC-MS (Method 3): $R_t$=1.71 min;
MS (ESIpos.): m/z (%)=713 (100) $[M+2H]^{2+}$, 1425 (10) $[M+H]^+$
MS (ESIneg.): m/z (%)=637 (100), 711 (80), 1423 (20) $[M-H]^-$.
HR-TOF-MS (Method 8): $C_{66}H_{105}N_6O_{19}$ ($MH^+$) calc. 1425.7742, fnd. 1425.7789;

For the amino acid sequence determination, an analytical sample of the product is hydrolysed according to General working procedure 3 and analysed (Method 7).

Examples 7 to 9

500 mg (0.35 mmol) of Example 2A are reacted according to General working procedure 2. After the reaction with 3-bromophenyl isocyanate, 202 mg of a mixture of several monosubstituted derivatives of Example 2A are isolated.
HPLC (Method 1): $R_t$=4.62 min;
LC-MS (Method 3): $R_t$=2.28 min;
MS (ESIpos.): m/z (%)=738 (100) $[M-Boc+2H]^{2+}$, 788 (5) $[M+2H]^{2+}$, 1574 (5) $[M+H]^+$;
MS (ESIneg.): m/z (%)=786 (100), 1573 (10) $[M-H]^-$.

The mixture is provided as a suspension in 6 ml of DCM, 2 ml of TFA are added and the mixture is stirred at RT for 15 min, until complete conversion is indicated by analytical HPLC (Method 1). The crude product is freed of solvent in vacuo. Finally, the crude product is coarsely purified by gel chromatography (Method 9; methanol:acetone:TFA/80:20:0.1) and finely purified and separated by means of preparative HPLC (Method 12). 105 mg (19% of th.) of Example 7, 51 mg (9% of th.) of Example 8 and 10 mg (2% of th.) of Example 9 are obtained.

Example 7

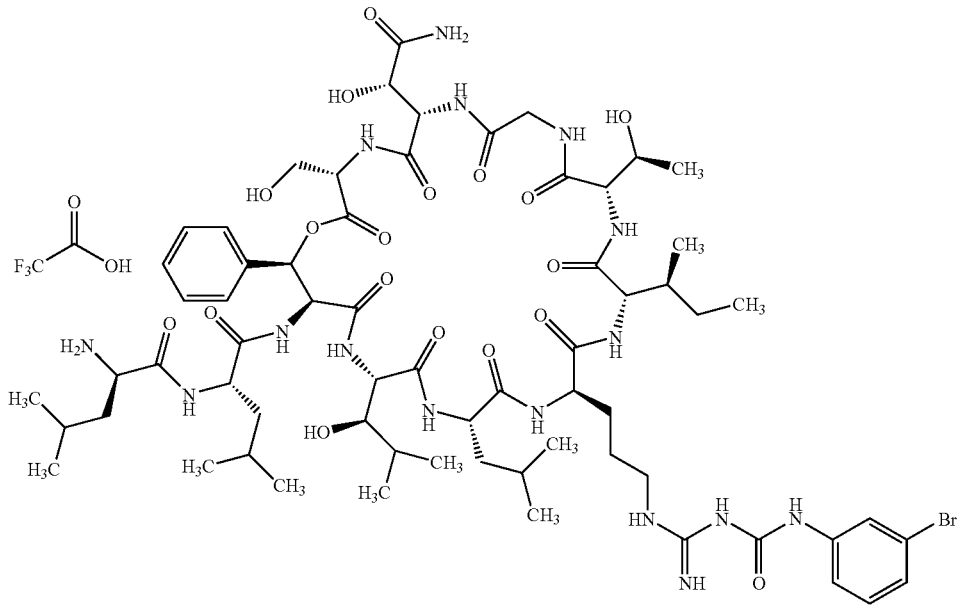

$N^{\omega,6}$-(3-Bromophenylaminocarbonyl)lysobactin trifluoroacetate

HPLC/UV-vis (Method 2): $R_t$=4.2 min.
$\lambda_{max}$ (qualitative)=220 (nm), 246 nm (w).
HPLC (Method 1): $R_t$=3.73 min
HPLC (Method 6): $R_t$=3.39 min
LC-MS (Method 3): $R_t$=1.61 min;
MS (ESIpos.): m/z (%)=652 (50), 738 (100) $[M+2H]^{2+}$, 1473 (10) $[M+H]^+$
MS (ESIneg.): m/z (%)=736 (100), 1471 (15) $[M-H]^-$.
HR-TOF-MS (Method 8): $C_{65}H_{102}N_{16}O_{18}$ ($MH^+$) calc. 1473.6741, fnd. 1473.6750.

For the amino acid sequence determination, an analytical sample of the product is hydrolysed according to General working procedure 3 and analysed (Method 7).

Example 8

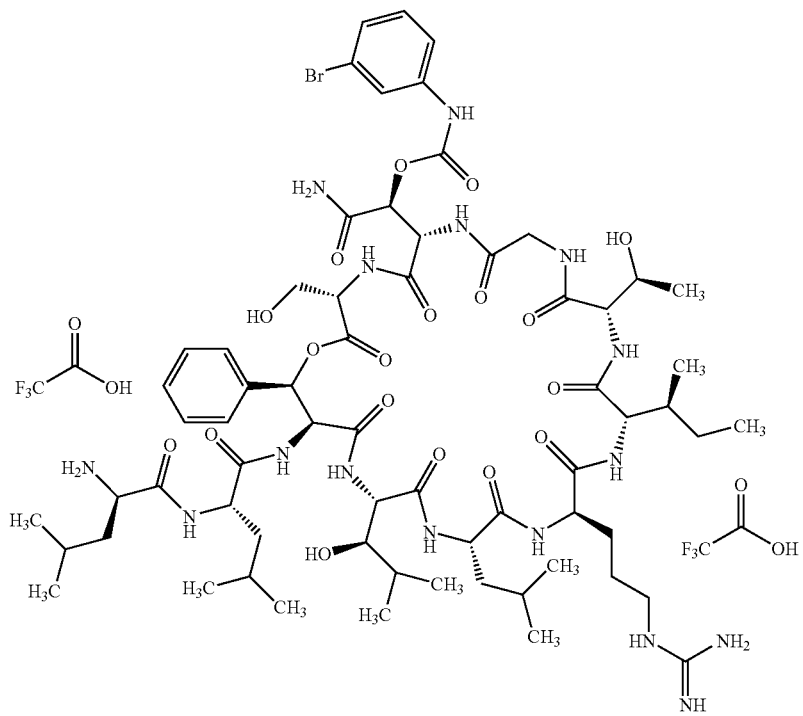

$O^{3.10}$-(3-Bromophenylaminocarbonyl)lysobactin bistrifluoroacetate

HPLC/UV-vis (Method 2): $R_t$=4.4 min.
$\lambda_{max}$ (qualitative)=200 (m), 240 nm (w).
HPLC (Method 1): $R_t$=3.86 min
HPLC (Method 6): $R_t$=4.82 min
LC-MS (Method 3): $R_t$=1.71 min;
MS (ESIpos.): m/z (%)=738 (100) [M+2H]$^{2+}$, 1473 (5) [M+H]$^+$ MS (ESIneg.): m/z (%)=637 (100), 736 (10), 1471 (5) [M−H]$^-$.

HR-TOF-MS (Method 8): $C_{65}H_{102}N_{16}O_{18}$ (MH$^+$) calc. 1473.6741, fnd. 1473.6781.

For the amino acid sequence determination, an analytical sample of the product is hydrolysed according to General working procedure 3 and analysed (Method 7).

TABLE 1

$^1$H-NMR (500 MHz, d$_5$-pyridine, 302K) and $^{13}$C-NMR (d$_5$-pyridine) data:

| Radical | NH | CO | CH-α | CH-β | CH-χ | Further radicals |
|---|---|---|---|---|---|---|
| Leu1 | — | 173.96 | 4.88 | 2.08; 2.21 | 2.02 | Me 0.97(22.87) |
|  |  |  | (52.70) | (42.06) | (25.31) | Me 0.86(21.58) |
| Leu2 | 11.17 | 176.82 | 4.51 | 1.84; 2.33 | 2.17 | Me 0.78(23.55) |
|  |  |  | (57.06) | (40.32) | (25.36) | Me 1.04(20.66) |
| Ph-Ser | 9.60 | 173.63 | 6.25 | 7.38 |  | Ph-o: 8.14(128.56) |
|  |  |  | (62.70) | (75.41) |  | Ph-m: 7.57(129.31) |
|  |  |  |  |  |  | Ph-p: 7.30(129.31) |
|  |  |  |  |  |  | Ph-i: 137.28 |

TABLE 1-continued $^1$H-NMR (500 MHz, $d_5$-pyridine, 302K) and $^{13}$C-NMR ($d_5$-pyridine) data:

| Radical | NH | CO | CH-α | CH-β | CH-χ | Further radicals |
|---|---|---|---|---|---|---|
| Hy-Leu | 9.37 | 173.65 | 4.33 (60.93) | 3.90 (75.50) | 2.39 (31.22) | Me 0.65(19.17) Me 1.07(20.17) |
| Leu3 | 7.94 | 174.33 | 5.11 (53.45) | 2.24 (42.21) | 2.45 (25.02) | Me 0.98(21.05) Me 1.10(24.41) |
| Arg | 7.69 | 173.39 | 4.61 (56.30) | 2.16; 2.21 (29.17) | 1.40; 2.14 (27.30) | CH$_2$-δ: 3.18; 3.34(41.49) NH-δ: 8.96 C=N: 158.26 |
| Ile | 8.26 | 172.71 | 4.69 (61.09) | 2.29 (36.69) | 1.30; 2.01 (26.90) | |
| Thr | 7.76 | 174.54 | 5.41 (58.64) | 4.38 (70.80) | | Me 1.72(22.02) |
| Gly | 11.02 | 169.45 | 4.01; 4.63 (44.82) | | | |
| Hy-Asn | 8.56 | 168.79 | 6.11 (55.80) | 6.50 (74.53) | | CONH$_2$ 170.68 O—CO—N 152.45 C-1 140.66 C-2 7.81(121.46) C-3 122.89 C-4 7.32(117.19) C-5 6.97(130.79) C-6 7.06(126.07) |
| Ser | 8.13 | 168.49 | 5.33 (56.42) | 4.12; 4.18 (62.85) | | |

Example 9

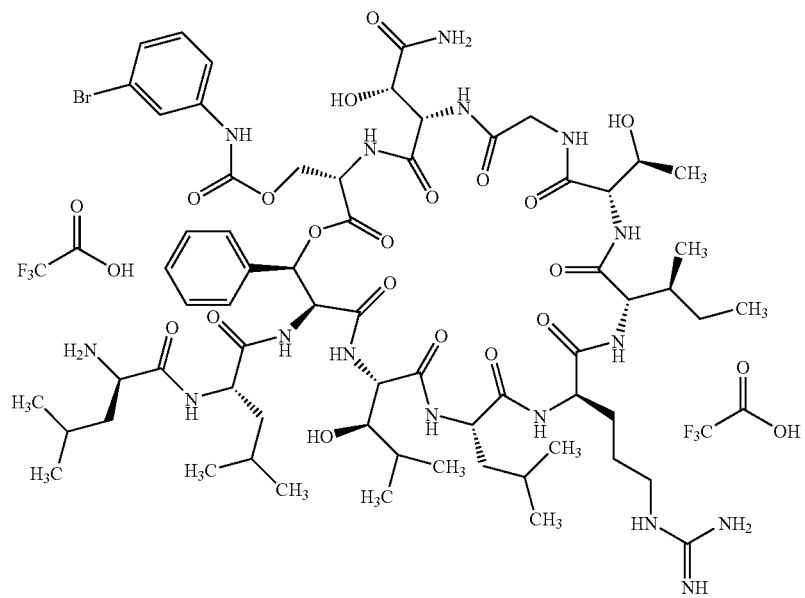

$O^{3,11}$-(3-Bromophenylaminocarbonyl)lysobactin bistrifluoroacetate

HPLC/UV-vis (Method 2): $R_t$=4.4 min.
$\lambda_{max}$ (qualitative)=200 (m), 240 nm (w).
HPLC (Method 1): $R_t$=3.92 min
HPLC (Method 6): $R_t$=6.01 min
LC-MS (Method 3): $R_t$=1.83 min;
MS (ESIpos.): m/z (%)=738 (100) [M+2H]$^{2+}$, 1473 (5) [M+H]$^+$ MS (ESIneg.): m/z (%)=637 (100), 736 (40), 1471 (10) [M−H]$^-$.
HR-TOF-MS (Method 8): $C_{65}H_{102}N_{16}O_{18}$ (MH$^+$) calc. 1473.6741, fnd. 1473.6766.

For the amino acid sequence determination, an analytical sample of the product is hydrolysed according to General working procedure 3 and analysed (Method 7).

Example 10

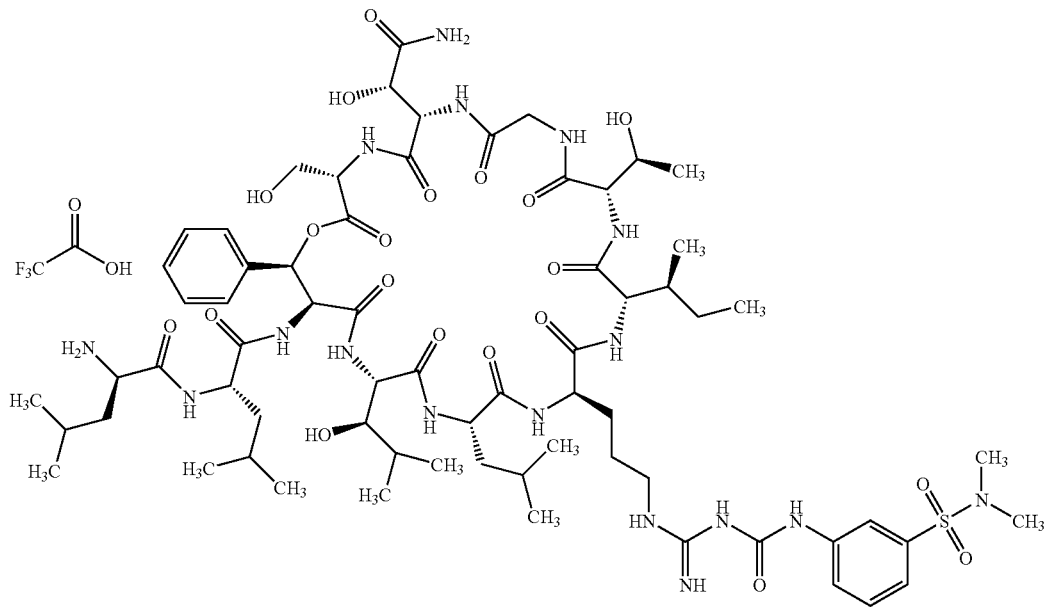

$N^{\omega,6}$-(3-(N,N-Dimethylsulfonyl)phenylaminocarbonyl)lysobactin trifluoroacetate 500 mg (0.35 mmol) of Example 2A are reacted according to General working procedure 2. After the reaction with 3-(N,N-dimethylsulfonyl)phenyl isocyanate, 40 mg of a mixture of several monosubstituted derivatives of Example 2A are isolated.

HPLC (Method 1): $R_t$=4.48 min;

HPLC (Method 2): $R_t$=5.0 min; LC-MS (Method 3): $R_t$=2.20 min;

MS (ESIpos.): m/z (%)=752 (100) [M-Boc+2H]$^{2+}$, 1602 (10) [M+H]$^+$;

MS (ESIneg.): m/z (%)=687 (100), 800 (35), 1600 (10) [M-H]$^-$);

HR-TOF-MS (Method 8): $C_{72}H_{116}N_{17}O_{22}$ (MH$^+$) calc. 1602.8202, fnd. 1602.8148).

The mixture is provided as a suspension in 6 ml of DCM, 2 ml of TFA are added and the mixture is stirred at RT for 15 min, until complete conversion is indicated by analytical HPLC (Method 1). The crude product is freed of solvent in vacuo. Finally, the crude product is coarsely purified by gel chromatography (Method 9; methanol:acetone:TFA/80:20:0.1) and finely purified and separated by means of preparative HPLC (Method 14). 12.5 mg (2% of th.) of the title compound (Example 10) are obtained.

HPLC/UV-vis (Method 2): $R_t$=4.2 min.

$\lambda_{max}$ (qualitative)=200 (m), 250 nm (w).

HPLC (Method 1): $R_t$=3.70 min;

LC-MS (Method 3): $R_t$=1.72 min;

MS (ESIpos.): m/z (%)=652 (60), 752 (100) [M+2H]$^{2+}$, 1502 (5) [M+H]$^+$

MS (ESIneg.): m/z (%)=637 (30), 750 (100), 1500 (10) [M-H]$^-$.

HR-TOF-MS (Method 8): $C_{67}H_{108}N_{17}O_{20}$ (MH$^+$) calc. 1502.7677, fnd. 1502.7721.

Examples 11 to 13

500 mg (0.35 mmol) of Example 2A are reacted according to General working procedure 2. After the reaction with 4-morpholinophenyl isocyanate, 66 mg of a mixture of several monosubstituted derivatives of Example 2A are isolated.

HPLC (Method 1): $R_t$=4.35 min;

HPLC (Method 2): $R_t$=4.7 min; $\lambda_{max}$(qualitative)=200 nm (s), 256 nm (m);

LC-MS (Method 3): $R_t$=2.37 min;

MS (ESIpos.): m/z (%)=741 (75) [M-Boc+2H]$^{2+}$, 791 (100) [M+2H]$^{2+}$;

MS (ESIneg.): m/z (%)=687 (50), 789 (100);

HR-TOF-MS (Method 8): $C_{74}H_{18}N_{17}O_{21}$ (MH$^+$) calc. 1580.8688, fnd. 1580.8671).

The mixture is provided as a suspension in 5 ml of DCM, 1.7 ml of TFA are added and the mixture is stirred at RT for 15 min, until complete conversion is indicated by analytical HPLC (Method 1). The crude product is freed of solvent in vacuo. Finally, the crude product is coarsely purified by gel chromatography (Method 9; methanol:acetone:TFA/80:20: 0.1) and finely purified and separated by means of preparative HPLC (Method 15). 5.7 mg (9% of th.) of Example 11, 3.7 mg (5% of th.) of Example 12 and 1.2 mg (2% of th.) of Example 13 are obtained.

Example 11

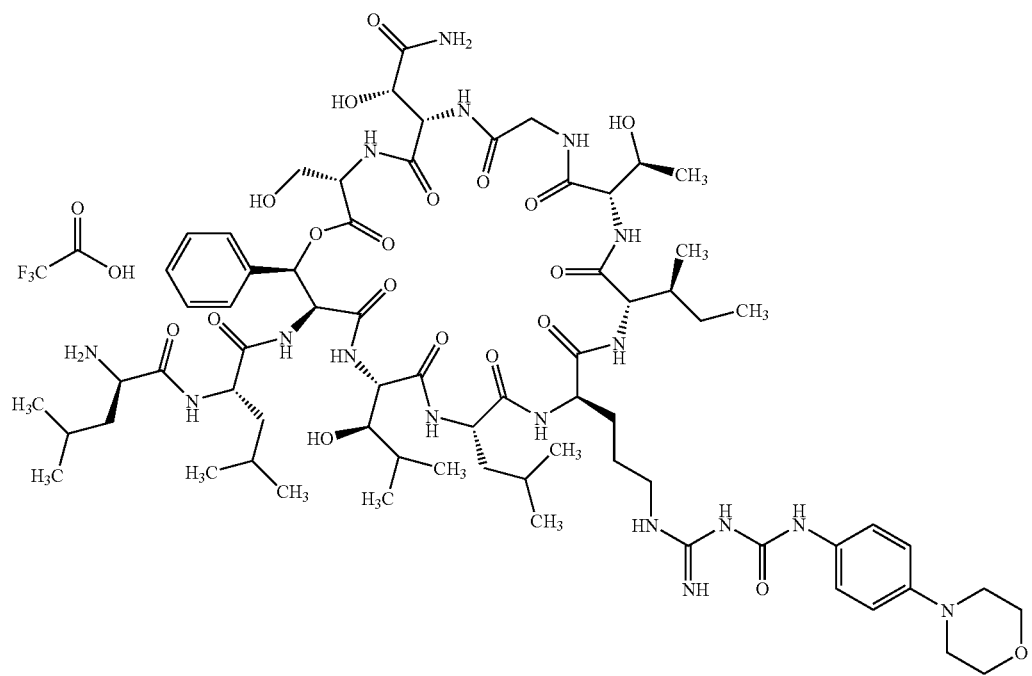

N$^{\omega,6}$-(4-Morpholinophenylaminocarbonyl)lysobactin trifluoroacetate

HPLC/UV-vis (Method 2): $R_t$=4.0 min.

$\lambda_{max}$ (qualitative)=200 nm (s), 246 nm (m).

HPLC (Method 1): $R_t$=3.62 min.

LC-MS (Method 3): $R_t$=1.55 min;

MS (ESIpos.): m/z (%)=741 (100) [M+2H]$^{2+}$, 1480 (5) [M+H]$^+$

MS (ESIneg.): m/z (%)=740 (100), 1478 (10) [M−H]$^-$.

HR-TOF-MS (Method 8): $C_{69}H_{110}N_{17}O_{19}$ (MH$^+$) calc. 1480.8164, fnd. 1480.8112.

For the amino acid sequence determination, an analytical sample of the product is hydrolysed according to General working procedure 3 and analysed (Method 7).

Example 12

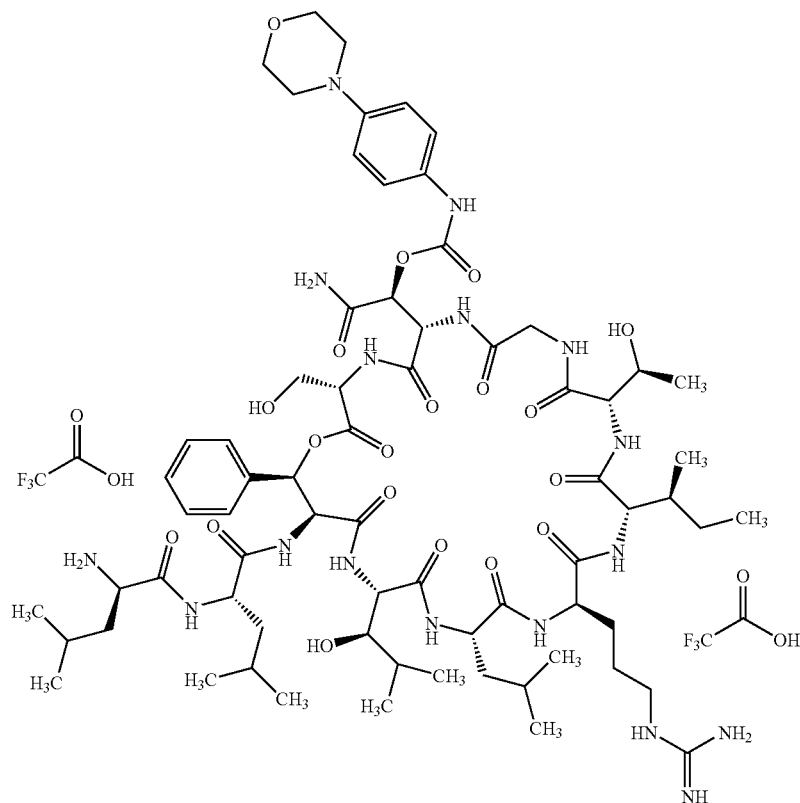

O$^{3.10}$-(4-Morpholinophenylaminocarbonyl)lysobactin bistrifluoroacetate

HPLC/UV-vis (Method 2): R$_t$=4.0 min.

λ$_{max}$ (qualitative)=200 nm (s), 246 nm (m).

HPLC (Method 1): R$_t$=3.66 min.

LC-MS (Method 3): R$_t$=1.63 min;

MS (ESIpos.): m/z (%)=741 (100) [M+2H]$^{2+}$, 1480 (5) [M+H]$^+$

MS (ESIneg.): m/z (%)=637 (100).

HR-TOF-MS (Method 8): C$_{69}$H$_{10}$N$_{17}$O$_{19}$ (MH$^+$) calc. 1480.8164, fnd. 1480.8188.

For the amino acid sequence determination, an analytical sample of the product is hydrolysed according to General working procedure 3 and analysed (Method 7).

Example 13

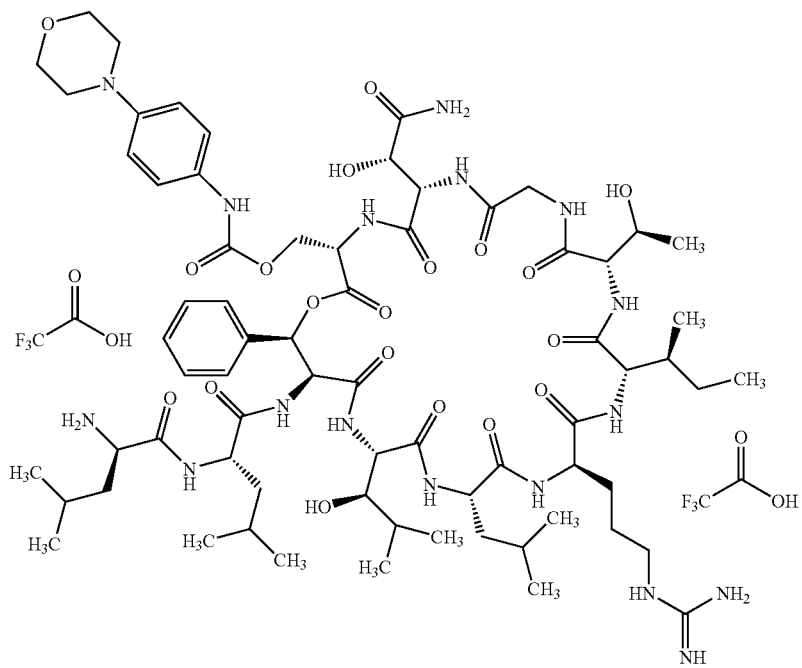

$O^{3.11}$-(3-Morpholinophenylaminocarbonyl)lysobactin bistrifluoroacetate

HPLC/UV-vis (Method 2): $R_t$=4.0 min.

$\lambda_{max}$ (qualitative)=200 (s), 242 nm (m).

HPLC (Method 1): $R_t$=3.66 mm

LC-MS (Method 3): $R_t$=1.73 min;

MS (ESIpos.): m/z (%)=494 (75), 741 (100) $[M+2H]^{2+}$.

HR-TOF-MS (Method 8): $C_{69}H_{110}N_{17}O_{19}$ ($MH^+$) calc. 1480.8164, fnd. 1480.8164.

For the amino acid sequence determination, an analytical sample of the product is hydrolysed according to General working procedure 3 and analysed (Method 7).

Examples 14 and 15

300 mg (0.21 mmol) of Example 2A are reacted according to General working procedure 1. After the reaction with phenylcarbonyl chloride, 221 mg of a mixture of two monosubstituted derivatives of Example 2A are isolated.

HPLC (Method 1): $R_t$=4.52 min;

LC-MS (Method 3): $R_t$=2.49 min;

MS (ESIpos.): m/z (%)=1480 (40) $[M+H]^+$.

The mixture is provided as a suspension in 3 ml DCM, 1 ml of TFA is added and the mixture is stirred at RT for 10 min, until complete conversion is indicated by analytical HPLC (Method 1). The crude product is freed of solvent in vacuo. Finally, the crude product is coarsely purified by gel chromatography (Method 9; methanol:acetone:TFA/80:20:0.1) and finely purified by means of preparative HPLC (Method 11). 163 mg (73% of th.) of Examples 14 and 15 are obtained as a 1:1 mixture.

HPLC (Method 1): $R_t$=3.88 min

LC-MS (Method 3): $R_t$=1.83 min;

MS (ESIpos.): m/z (%)=199 (100), 691 (50), 1380 (10) $[M+H]^+$

For the amino acid sequence determination, an analytical sample of the product is hydrolysed according to General working procedure 3 and analysed (Method 7) (1/1 mixture).

Example 14
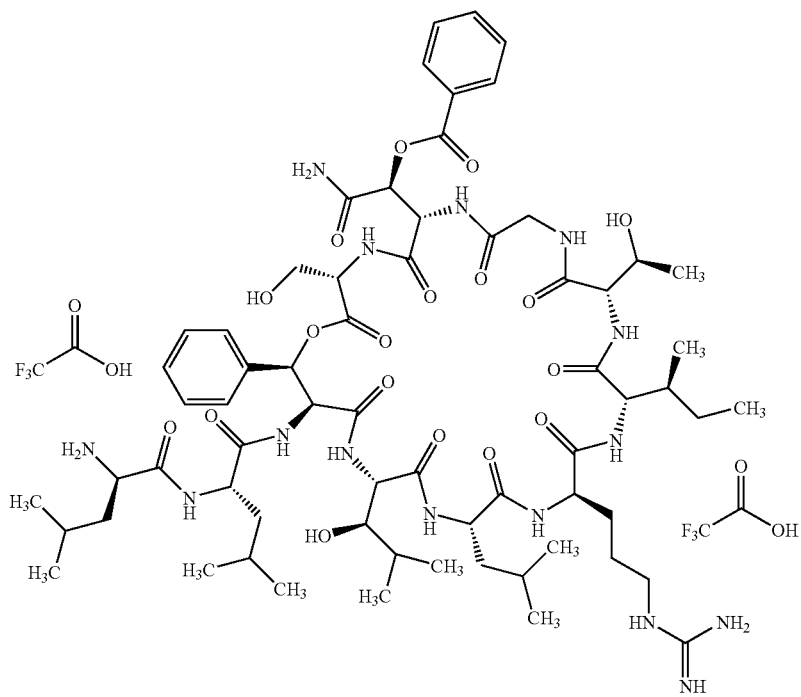
$O^{3.10}$-(Phenylcarbonyl)lysobactin bistrifluoroacetate
Example 15
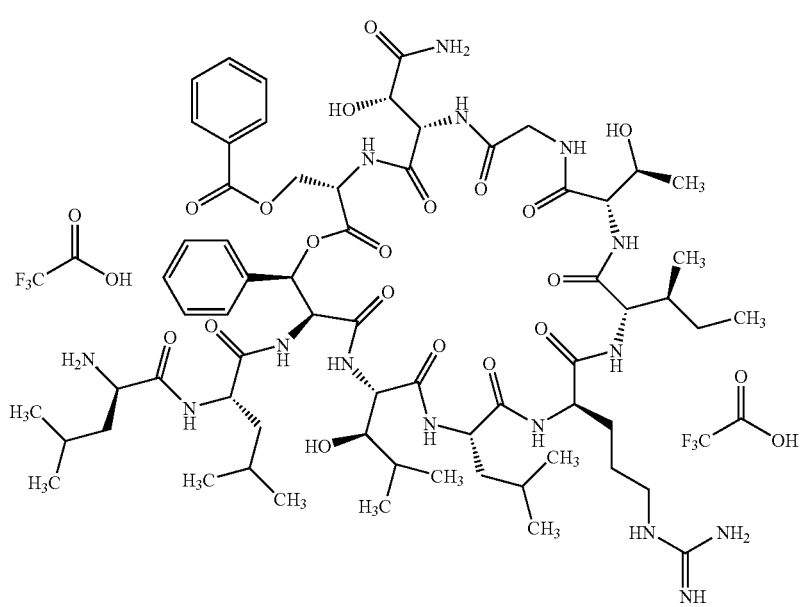
$O^{3.11}$-(Phenylcarbonyl)lysobactin bistrifluoroacetate

Example 16

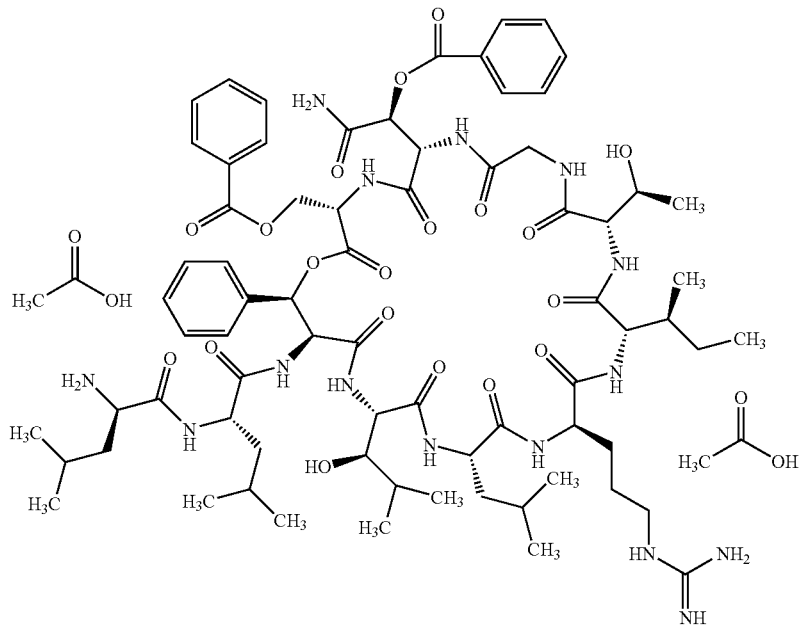

$O^{3.10}$, $O^{3.11}$-Di(phenylcarbonyl)lysobactin bisacetate 23 mg (0.02 mmol) of Example 2A are reacted according to General working procedure 1. After the reaction with phenylcarbonyl chloride, in addition to the two monosubstituted Boc-protected lysobactin derivatives (Examples 14 and 15), 3.2 mg of a compound having two benzoyl groups are isolated in this reaction.

HPLC (Method 1): $R_t$=4.81 min;

LC-MS (Method 3): $R_t$=2.52 min;

MS (ESIpos.): m/z (%)=743 (100), 1584 (5) [M+H]$^+$;

MS (ESIneg.): m/z (%)=121 (10), 1582 (5) [M−H]$^-$.

The mixture is provided as a suspension in 0.15 ml of DCM, 0.05 ml of TFA are added and the mixture is stirred at RT for 6 min until complete conversion is indicated by analytical HPLC (Method 1). The crude product is freed of solvent in vacuo. Finally, the crude product is separated by gel chromatography (Method 9; methanol:acetone:acetic acid/ 80:20:0.1). 1.7 mg (6.5% of th.) of the title compound are obtained.

HPLC (Method 1): $R_t$=3.88 min.

LC-MS (Method 3): $R_t$=1.98 min;

MS (ESIpos.): m/z (%)=743 (100) [M+2H]$^{2+}$;

MS (ESIneg.): m/z (%)=121(100), 741 (40).

For the amino acid sequence determination, an analytical sample of the product is hydrolysed according to General working procedure 3 and analysed (Method 7).

Example 17

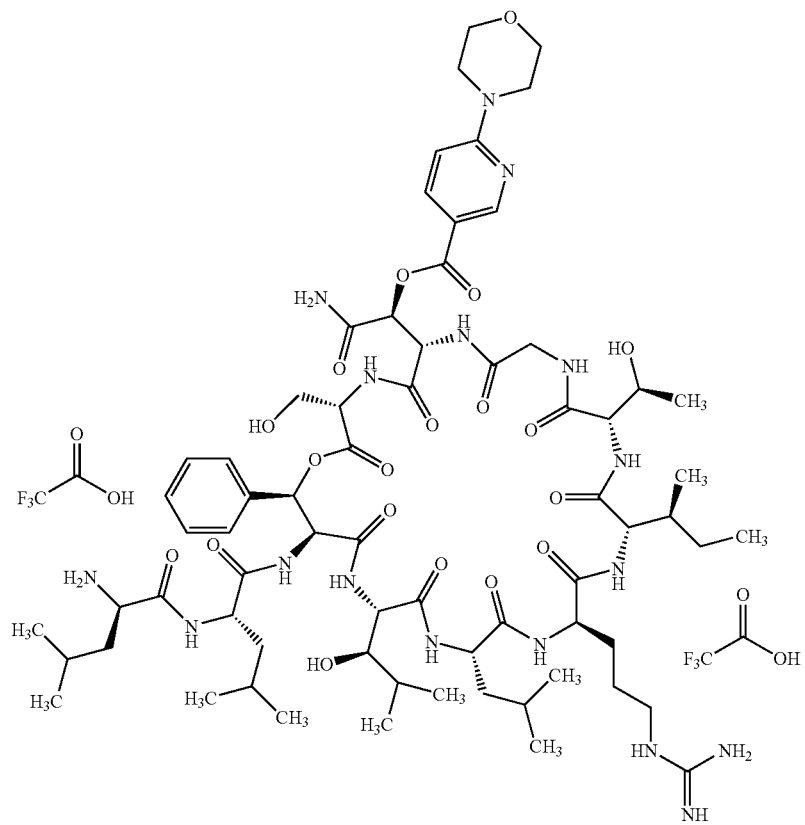

O$^{3.10}$-(3-(6-Morpholino-3-pyridyl)carbonyl)lysobactin bistrifluoroacetate 500 mg (0.35 mmol) of Example 2A are reacted according to General working procedure 1. After the reaction with 6-(morpholin-4-yl)pyridine-3-carbonyl chloride, 151 mg of a monosubstituted derivative of Example 2A are isolated.

HPLC (Method 1): R$_t$=4.38 min;

LC-MS (Method 3): R$_t$=2.07 min;

MS (ESIpos.): m/z (%)=734 (20) [M-Boc+2H]$^{2+}$, 784 (100) [M+2H]$^{2+}$, 1566 (100) [M+H]$^+$;

MS (ESIneg.): m/z (%)=782 (100), 1564 (100) [M–H]$^-$).

The Boc-protected lysobactin derivative is provided as a suspension in 3 ml of DCM, 1 ml of TFA is added and the mixture is stirred at RT for 15 min, until complete conversion is indicated by analytical HPLC (Method 1). The crude product is freed of solvent in vacuo. Finally, the crude product is finely purified by means of preparative HPLC (Method 11). 135 mg (23% of th.) of the title compound (Example 17) are obtained.

HPLC (Method 1): R$_t$=3.64 min.

HPLC (Method 4): R$_t$=7.98 min.

LC-MS (Method 3): R$_t$=1.60 min;

MS (ESIpos.): m/z (%)=734 (100) [M+2H]$^{2+}$, 1466 (2) [M+H]$^+$

MS (ESIneg.): m/z (%)=628 (100), 732 (50), 1464 (10) [M–H]$^-$.

HR-TOF-MS (Method 8): C$_{68}$H$_{108}$N$_{17}$O$_{19}$ (MH$^+$) calc. 1466.8007, fnd. 11466.7960.

For the amino acid sequence determination, an analytical sample of the product is analysed (Method 18).

Examples 18 and 19

500 mg (0.35 mmol) of Example 2A are reacted according to General working procedure 1. After the reaction with 3-methoxyphenylcarbonyl chloride, 115 mg of a mixture of two monosubstituted derivatives of Example 2A are isolated.

HPLC (Method 1): R$_t$=4.58 min;

LC-MS (Method 3): R$_t$=2.24 min;

MS (ESIpos.): m/z (%)=706 (100), 1510 (20) [M+H]$^+$;

MS (ESIneg.): m/z (%)=754 (100), 1508 (20) [M–H]$^-$.

The mixture is provided as a suspension in 3 ml of DCM, 1 ml of TFA is added and the mixture is stirred at RT for 25 min, until complete conversion is indicated by analytical HPLC (Method 1). The crude product is freed of solvent in vacuo. Finally, the crude product is coarsely purified by gel chromatography (Method 9; methanol:acetone:TFA/80:20:0.1) and finely purified by means of preparative HPLC (Method 16). 3 mg (0.7% of th.) of Examples 18 and 19 are obtained as a 1:1 mixture.

HPLC (Method 1): R$_t$=3.79 min.

HPLC (Method 5): R$_t$=7.56 min

LC-MS (Method 3): R$_t$=1.63 min;

MS (ESIpos.): m/z (%)=706 (100), 1410 (10) [M+H]$^+$

MS (ESIneg.): m/z (%)=704 (60), 1408 (15) [M–H]$^-$.

For the amino acid sequence determination, an analytical sample of the product is hydrolysed according to General working procedure 3 and analysed (Method 7) (1/1 mixture).

Example 18
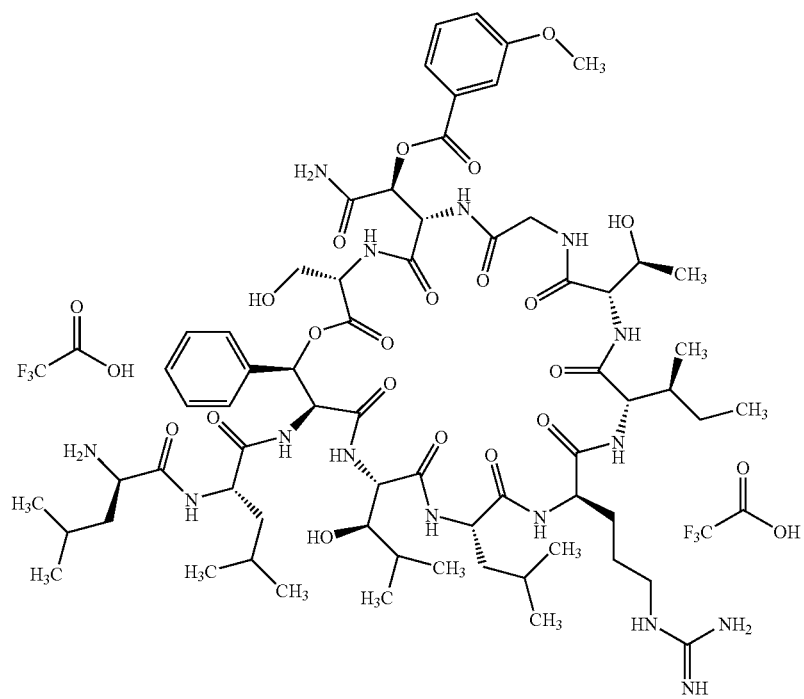
O[3.10]-(3-Methoxyphenylcarbonyl)lysobactin bistrifluoroacetate
Example 19
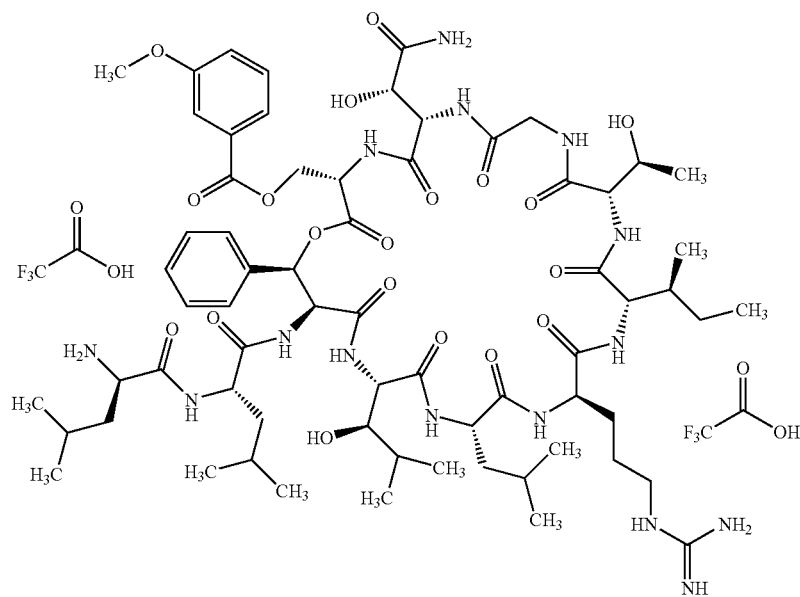
O[3.11]-(Methoxyphenylcarbonyl)lysobactin bistrifluoroacetate Example 20

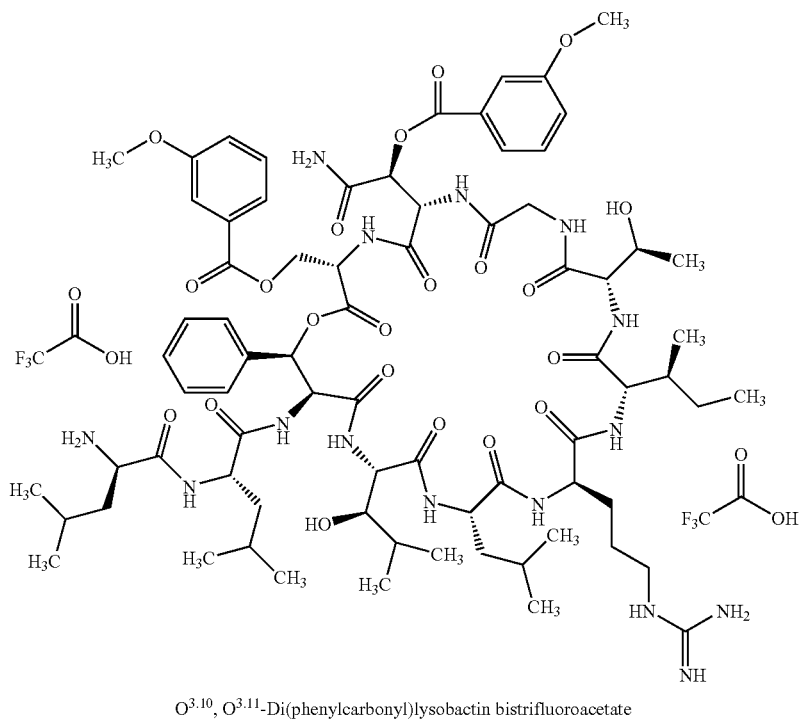

$O^{3,10}$, $O^{3,11}$-Di(phenylcarbonyl)lysobactin bistrifluoroacetate 53 mg (0.035 mmol) of Example 2A are reacted according to General working procedure 1. After the reaction with 3-methoxyphenylcarbonyl chloride, in addition to the two monosubstituted derivatives of Example 2A (Example 18 and 19) 11 mg of a compound having two benzoyl groups are isolated in this reaction.

HPLC (Method 1): $R_t$=4.88 min;

LC-MS (Method 3): $R_t$=2.62 min;

MS (ESIpos.): m/z (%)=773 (45), 823 (100), 1644 (15).

The mixture is provided as a suspension in 1 ml of DCM, 0.3 ml of TFA are added and the mixture is stirred at RT for 15 min, until complete conversion is indicated by analytical HPLC (Method 1). The crude product is freed of solvent in vacuo. Finally, the crude product is finely purified by gel chromatography (Method 9; methanol:acetone:TFA/80:20: 0.5). 6.2 mg (116% of th.) of the title compound are obtained.

HPLC (Method 1): $R_t$=4.00 min.

LC-MS (Method 3): $R_t$=1.96 min;

MS (ESIpos.): m/z (%)=773 (100), 1544 (10) $[M+2H]^{2+}$;

MS (ESIneg.): m/z (%)=151 (100), 1542 (20).

For the amino acid sequence determination, an analytical sample of the product is hydrolysed according to General working procedure 3 and analysed (Method 7).

Example 21

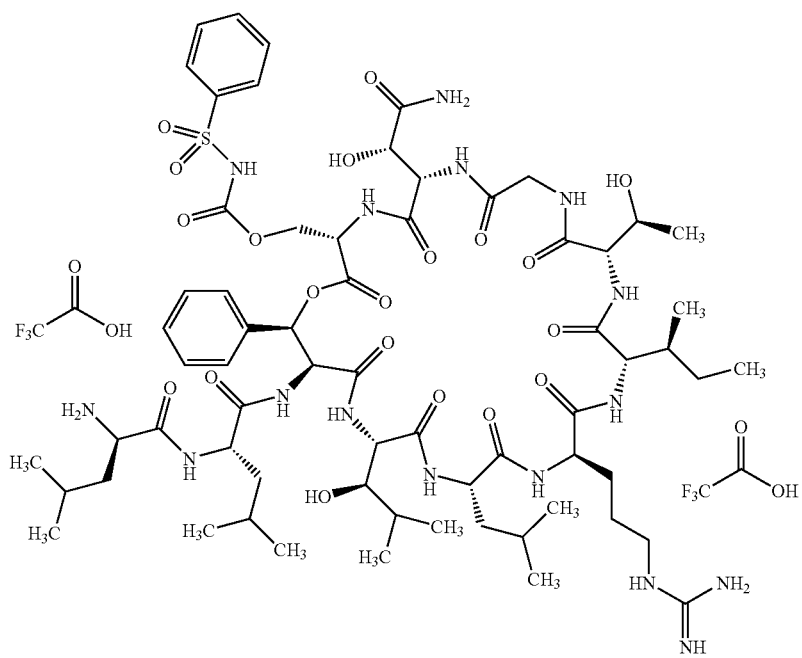

O$^{3.11}$-(Phenylsulfonylaminocarbonyl)lysobactin bistrifluoroacetate 500 mg (0.35 mmol) of Example 2A are reacted according to General working procedure 2. After the reaction with phenylsulfonyl isocyanate, 318 mg of a monosubstituted Boc-protected lysobactin derivative are isolated.

HPLC (Method 1): R$_t$=4.56 min;
LC-MS (Method 3): R$_t$=2.45 min;
MS (ESIpos.): m/z (%)=730 (100) [M-Boc+2H]$^{2+}$, 1559 (20) [M+H]$^+$;
MS (ESIneg.): m/z (%)=778 (100), 1557 (50) [M-H]$^-$);
HR-TOF-MS (Method 8): C$_{70}$H$_{111}$N$_{16}$O$_{22}$S (MH$^+$) calc. 1559.7780, fnd. 1559.7739.

The crude product is provided as a suspension in 9 ml of DCM, 3 ml of TFA are added and the mixture is stirred at RT for 10 min, until complete conversion is indicated by analytical HPLC (Method 1). The crude product is freed of solvent in vacuo. Finally, the crude product is coarsely purified by gel chromatography (Method 9; methanol:acetone:TFA/80:20: 0.1) and finely purified by means of preparative HPLC (Method 17). 218 mg (43% of th.) of the title compound (Example 21) are obtained.

HPLC (Method 1): R$_t$=3.86 min.
HPLC/UV-vis (Method 2): R$_t$=4.23 min.
λ$_{max}$ (qualitative)=200 nm (s), 220 nm (m).
LC-MS (Method 3): R$_t$=2.00 min;
MS (ESIpos.): m/z (%)=730 (100) [M+2H]$^{2+}$, 1459 (5) [M+H]$^+$;
MS (ESIneg.): m/z (%)=728 (100), 1457 (80) [M-H]$^-$.
HR-TOF-MS (Method 8): C$_{65}$H$_{103}$N$_{16}$O$_{20}$ (MH$^+$) calc. 1459.7255, fnd. 1459.7209.

For the amino acid sequence determination, an analytical sample of the product is hydrolysed according to General working procedure 3 and analysed (Method 18).

B. Evaluation of the Physiological Activity

The in vitro activity of the compounds of the invention can be shown in the following assays:

Determination of the Minimum Inhibitory Concentration (MIC):

The MIC is determined in the liquid dilution test in accordance with the NCCLS guidelines. Overnight cultures of *Staphylococcus aureus* 133, *Entercococcus faecalis* 27159, *E. faecium* 4147 and *Streptococcus pneumoniae* G9a are incubated with the described test substances in a 1:2 dilution series. The MIC determination is carried out with a cell count of 10$^5$ microorganisms per ml in Isosensitest medium (Difco, Irvine/USA), with the exception of *S. pneumoniae*, which is tested in BHI broth (Difco, Irvine/USA) with 10% bovine serum at a cell count of 10$^6$ microorganisms per ml. The cultures are incubated at 37° C. for 18-24 hours, *S. pneumoniae* in the presence of 10% CO$_2$.

The lowest substance concentration in each case at which no visible bacterial growth occurs any more is defined as the MIC. The MIC values are reported in μg/ml.

Representative in-vitro activity data for the compounds of the invention are shown in

TABLE A

| Example No. | MIC S. aureus 133 [μg/ml] | MIC S. pneumoniae G9a [μg/ml] | MIC E. faecium L4001 [μg/ml] | MIC E. faecalis ICB 27159 [μg/ml] |
|---|---|---|---|---|
| 2 | 0.5 | 1 | 4 | 1 |
| 11 | 0.5 | 0.5 | 1 | 0.5 |

TABLE A-continued

| Example No. | MIC S. aureus 133 [µg/ml] | MIC S. pneumoniae G9a [µg/ml] | MIC E. faecium L4001 [µg/ml] | MIC E. faecalis ICB 27159 [µg/ml] |
|---|---|---|---|---|
| 14/15 | 0.4 | 0.8 | 3.2 | 1.6 |
| 17 | 0.5 | 0.5 | 4 | 2 |

The suitability of the compounds of the invention for the treatment of bacterial infections can be shown in the following animal model:

Systemic Infection with *Staphylococcus aureus* 133:

Cells of *S. aureus* 133 are grown overnight in BHI broth (Oxoid, N.Y./USA). The overnight culture is diluted 1:100 in fresh BHI broth and incubated for 3 hours. The cells which are then in the logarithmic growth phase are centrifuged off and washed twice with buffered, physiological saline. A cell suspension in saline is then adjusted photometrically to an extinction of 50 units. After a dilution step (1:15), this suspension is mixed 1:1 with a 10% mucin solution. 0.25 ml/20 g mouse of this infection solution are administered intraperitoneally (corresponding to $1 \times 10^6$ microorganisms/mouse). The therapy takes place intraperitoneally or intravenously 30 minutes after infection. Female CFW1 mice are used for the infection experiment. The survival of the animals is recorded over a period of 6 days.

The properties of the compounds of the invention with respect to the renal tolerability can be shown in the following animal model:

Mouse Model for the Determination of Nephrotoxic Effects:

Nephrotoxic side effects of the nonadepsipeptides are analysed by histopathological examinations of the kidneys in mice and/or rats after multiple administration of a particular dosage. For this, 5-6 animals are treated daily either intravenously (i.v.) or intraperitoneally (i.p.) with substances which are dissolved in an aqueous solution or with addition of Solutol. Nephrotoxic effects are determined by light-microscopical assessment of haematoxilin and eosin (H&E) stained paraffin sections of the kidneys. A periodic acid Schiff (PAS) reaction is optionally carried out for a better visualization of glycoproteins. Nephrotoxic effects are defined semiquantitatively for each animal as the degrees of severity of the tubular basophilia and degeneration/regeneration occurring (degrees of severity: 0=no effect; 1=minimal effect; 2=slight effect; 3=moderate effect; 4=severe lesions). The average degree of severity of the tubular degeneration/regeneration and the incidence (number of affected animals) is calculated for each animal group or derivative. Kidney changes going beyond this such as tubular dilatation and necrosis as well as the accumulation of necrotic materials are likewise listed.

The solubility of a compound is determined according to the methods known to the person skilled in the art.

C. Exemplary Embodiments of Pharmaceutical Compositions

The compounds of the invention can be converted into pharmaceutical preparations in the following ways:

Tablet:
Composition:
100 mg of the compound of Example 1, 50 mg of lactose (monohydrate), 50 mg of maize starch (native), 10 mg of polyvinylpyrolidone (PVP 25) (BASF, Ludwigshafen, Germany) and 2 mg of magnesium stearate.

Tablet weight 212 mg. Diameter 8 mm, radius of curvature 12 mm.

Preparation:
The mixture of active compound, lactose and starch is granulated with a 5% solution (m/m) of the PVP in water. The granules are dried and then mixed with the magnesium stearate for 5 min. This mixture is compressed using a conventional tablet press (see above for format of the tablet). A guideline for the compressive force used for the compression is 15 kN.

Suspension which can be Administered Orally:
Composition:
1000 mg of the compound of Example 1, 1000 mg of ethanol (96%), 400 mg of Rhodigel (xanthan gum from FMC, Pennsylvania, USA) and 99 g of water.

10 ml of oral suspension correspond to a single dose of 100 mg of the compound of the invention.

Preparation:
The Rhodigel is suspended in ethanol, and the active compound is added to the suspension. The water is added while stirring. The mixture is stirred for about 6 h until the swelling of the Rhodigel is complete.

Solution which can be Administered Intravenously:
Composition:
100-200 mg of the compound of Example 1, 15 g of polyethylene glycol 400 and 250 g of water for injection.

Preparation:
The compound of Example 1 is dissolved together with polyethylene glycol 400 in the water with stirring. The solution is sterilized by filtration (pore diameter 0.22 µm) and dispensed under aseptic conditions into heat-sterilized infusion bottles. The latter are closed with infusion stoppers and crimped caps.

What is claimed is:

1. A compound of formula

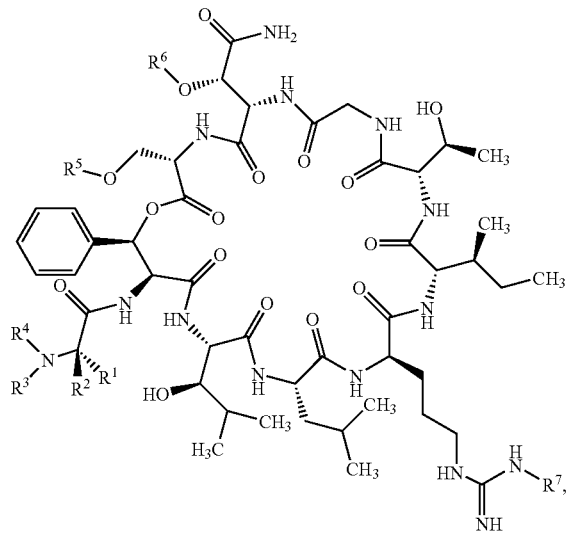

(I)

in which

R¹ represents hydrogen, $C_1$-$C_6$-alkyl, $C_2$-$C_6$-alkenyl, $C_3$-$C_6$-cycloalkyl or $C_6$-$C_{10}$-aryl, whereby alkyl, alkenyl, cycloalkyl and aryl can be substituted with 0, 1, 2 or 3 substituents selected independently of one another from the group consisting of halogen, hydroxy, amino, cyano, trimethylsilyl, $C_1$-$C_6$-alkyl, $C_1$-$C_6$-alkoxy, benzyloxy, $C_3$-$C_6$-cycloalkyl, $C_6$-$C_{10}$-aryl, 5- to 7-membered heterocyclyl, 5- to 10-membered heteroaryl, $C_1$-$C_6$-alkylamino, $C_6$-$C_{10}$-arylamino, $C_1$-$C_6$-alkylcarbonylamino, $C_6$-$C_{10}$-arylcarbonylamino, $C_1$-$C_6$-alkylcarbonyl, $C_1$-$C_6$-alkoxycarbonyl, $C_6$-$C_{10}$-arylcarbonyl and benzyloxycarbonylamino, wherein cycloalkyl, aryl, heterocyclyl and heteroaryl for their part can be substituted with 0, 1, 2 or 3 substituents selected independently of one another from the group consisting of halogen, hydroxy, amino, cyano, nitro, trifluoromethyl, $C_1$-$C_6$-alkyl, $C_1$-$C_6$-alkoxy, phenyl and 5- to 7-membered heterocyclyl, R² represents hydrogen or $C_1$-$C_4$-alkyl, R³ represents $C_1$-$C_6$-alkyl, $C_3$-$C_6$-cycloalkyl, 5- to 7-membered heterocyclyl, $C_6$-$C_{10}$-aryl, 5- or 6-membered heteroaryl, $C_1$-$C_6$-alkylcarbonyl, $C_1$-$C_6$-alkoxycarbonyl, $C_3$-$C_6$-cycloalkylcarbonyl, 5- to 7-membered heterocyclylcarbonyl, $C_6$-$C_{10}$-arylcarbonyl, 5- or 6-membered heteroarylcarbonyl or $C_1$-$C_6$-alkylaminocarbonyl, whereby alkyl, cycloalkyl, heterocyclyl, aryl, heteroaryl, alkoxycarbonyl, cycloalkylcarbonyl, heterocyclylcarbonyl, arylcarbonyl, heteroarylcarbonyl and alkylaminocarbonyl can be substituted with 0, 1, 2 or 3 substituents selected independently of one another from the group consisting of halogen, hydroxy, amino, $C_1$-$C_6$-alkylamino and phenyl, and whereby alkylcarbonyl is substituted with a substituent amino or $C_1$-$C_6$-alkylamino, and whereby alkylcarbonyl can be substituted with a further 0, 1 or 2 substituents selected independently of one another from the group consisting of halogen, hydroxy, trimethylsilyl, $C_1$-$C_6$-alkoxy, $C_1$-$C_6$-alkylthio, benzyloxy, $C_3$-$C_6$-cycloalkyl, phenyl, naphthyl, 5- to 10-membered heteroaryl, $C_1$-$C_6$-alkylcarbonylamino, $C_1$-$C_6$-alkoxycarbonylamino, $C_6$-$C_{10}$-arylcarbonylamino, $C_6$-$C_{10}$-arylcarbonyloxy, benzyloxycarbonyl and benzyloxycarbonylamino, wherein phenyl and heteroaryl for their part can be substituted with 0, 1, 2 or 3 substituents selected independently of one another from the group consisting of halogen, hydroxy, nitro, $C_1$-$C_6$-alkyl, $C_1$-$C_6$-alkoxy and phenyl, R⁴ represents hydrogen, $C_1$-$C_4$-alkyl, cyclopropyl or cyclopropylmethyl, and, either R⁵ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, and R⁶ represents hydrogen, and R⁷ represents hydrogen, or R⁵ represents hydrogen, and R⁶ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, and R⁷ represents hydrogen, or R⁵ represents hydrogen, and R⁶ represents hydrogen, and R⁷ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, or $R^5$ and $R^6$ are identical, and represent $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, and $R^7$ represents hydrogen, or one of its salts.

2. The compound of claim 1, whereby $R^1$ represents 2-methylprop-1-yl, 2,2-dimethylprop-1-yl, 2-pyridylmethyl or 3-pyridylmethyl, whereby 2-pyridylmethyl or 3-pyridylmethyl can be substituted with 0, 1, 2 or 3 substituents selected independently of one another from the group consisting of hydroxy, amino, trifluoromethyl, methyl, methoxy and morpholinyl, $R^2$ represents hydrogen, $R^3$ represents 1-amino-3-methylbut-1-ylcarbonyl, 1-amino-3,3-dimethylbut-1-ylcarbonyl or 1-amino-2-trimethylsilyleth-1-ylcarbonyl, $R^4$ represents hydrogen, and either $R^5$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, and $R^6$ represents hydrogen, and $R^7$ represents hydrogen, or $R^5$ represents hydrogen, and $R^6$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, and $R^7$ represents hydrogen, or $R^5$ represents hydrogen, and $R^6$ represents hydrogen, and $R^7$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, or $R^5$ and $R^6$ are identical, and represent $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, and $R^7$ represents hydrogen, or one of its salts.

3. The compound of claim 1, whereby $R^1$ represents 2-methylprop-1-yl, $R^2$ represents hydrogen, $R^3$ represents 1-amino-3-methylbut-1-ylcarbonyl, $R^4$ represents hydrogen, and either $R^5$ represents hydrogen, and $R^6$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, $C_6$-$C_{10}$-arylsulfonylaminocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, arylsulfonylaminocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, and $R^7$ represents hydrogen, or $R^5$ represents hydrogen, and $R^6$ represents hydrogen, and $R^7$ represents $C_6$-$C_{10}$-arylaminocarbonyl, $C_6$-$C_{10}$-arylcarbonyl, $C_6$-$C_{10}$-arylaminothiocarbonyl, $C_6$-$C_{10}$-arylthiocarbonyl, 5- to 10-membered heteroarylaminocarbonyl, 5- to 10-membered heteroarylcarbonyl, 5- to 10-membered heteroarylaminothiocarbonyl or 5- to 10-membered heteroarylthiocarbonyl, whereby arylaminocarbonyl, arylcarbonyl, arylaminothiocarbonyl, arylthiocarbonyl, heteroarylaminocarbonyl, heteroarylcarbonyl, heteroarylaminothiocarbonyl and heteroarylthiocarbonyl can be substituted with 0, 1, 2 or 3 substituents selected independently of one another from the group consisting of halogen, $C_1$-$C_6$-alkyl, $C_1$-$C_6$-alkoxy, $C_1$-$C_6$-alkylamino, $C_1$-$C_6$-alkoxycarbonyl, $C_1$-$C_6$-alkylaminocarbonyl, $C_1$-$C_6$-alkylaminosulfonyl, optionally oxo-substituted 5- to 7-membered heterocyclyl and 5- to 10-membered heteroaryl, or one of its salts.

4. The compound of claim 1, whereby $R^1$ represents 2-methylprop-1-yl, $R^2$ represents hydrogen, $R^3$ represents 1-amino-3-methylbut-1-ylcarbonyl, $R^4$ represents hydrogen, and either $R^5$ represents hydrogen, and $R^6$ represents phenylaminocarbonyl, phenylcarbonyl, pyridylaminocarbonyl or pyridylcarbonyl, whereby phenylaminocarbonyl, phenylcarbonyl, pyridylaminocarbonyl and pyridylcarbonyl can be substituted with 0, 1, 2 or 3 substituents selected independently of one another from the group consisting of pyrrolidinyl, piperidinyl, tetrahydropyranyl, piperazinyl, morpholinyl, 2-oxopyrrolidinyl and 2-oxopiperidinyl, and $R^7$ represents hydrogen, or $R^5$ represents hydrogen, and $R^6$ represents hydrogen, and $R^7$ represents phenylaminocarbonyl, phenylcarbonyl, pyridylaminocarbonyl or pyridylcarbonyl, whereby phenylaminocarbonyl, phenylcarbonyl, pyridylaminocarbonyl and pyridylcarbonyl can be substituted with 0, 1, 2 or 3 substituents selected independently of one another from the group consisting of pyrrolidinyl, piperidinyl, tetrahydropyranyl, piperazinyl, morpholinyl, 2-oxopyrrolidinyl and 2-oxopiperidinyl, or one of its salts.

5. The compound of claim 1 for the treatment of infections with Gram-positive bacteria.

6. A medicament comprising a compound of claim 1 in combination with an inert, non-toxic, pharmaceutically suitable excipient.

7. The medicament of claim 6 for the treatment of infections with Gram-positive bacteria.

8. A method for preparing a compound of formula (I) of claim 1, whereby a compound of formula

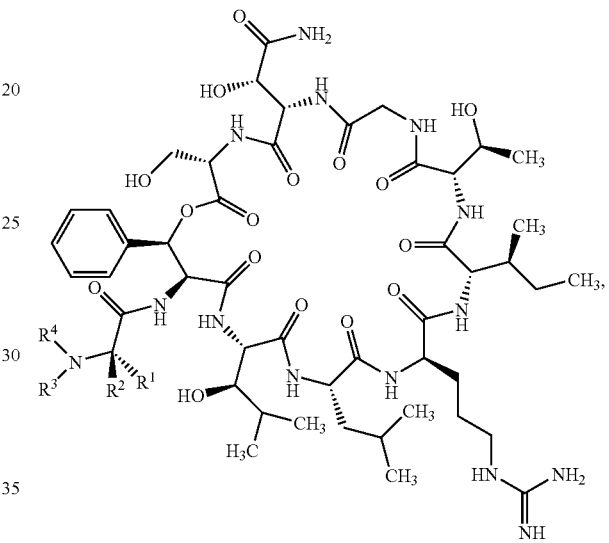

(II)

in which $R^1$, $R^2$, $R^3$ and $R^4$ have the meaning indicated in claim 1, is reacted with 1 to 10 equivalents of an aryl- or heteroarylcarbonyl chloride, of an aryl or heteroaryl isocyanate, of an aryl- or heteroarylthiocarbonyl chloride, of an aryl or heteroaryl isothiocyanate or of an arylsulfonyl isocyanate, whereby the aryl and heteroaryl radicals correspond to the aryl and heteroaryl radicals in the radicals $R^5$, $R^6$ and $R^7$, which have the meaning indicated in claim 1, and subsequently the resulting mixture of compounds of formula (I) is separated by chromatography into the individual compounds of formula (I).

9. A method for the production of a medicament comprising mixing a compound of claim 1 with an inert non-toxic pharmaceutically suitable excipient.

10. A method for treating infections with Gram-positive bacteria in humans and animals comprising administering an antibacterially effective amount of at least one compound of claim 1 to a human or animal in need thereof.

11. A method for treating infections with Gram-positive bacteria in humans and animals comprising administering an antibacterially effective amount of at least one medicament of claim 6 to a human or animal in need thereof.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: synthetically constructed peptide

<400> SEQUENCE: 1

Tyr Gly Gly Phe Leu
1               5